(12) United States Patent
Mower

(10) Patent No.: US 8,761,905 B2
(45) Date of Patent: Jun. 24, 2014

(54) METHODS, APPARATUS, AND SYSTEMS FOR MULTIPLE STIMULATION FROM A SINGLE STIMULATOR

(75) Inventor: Morton M. Mower, Baltimore, MD (US)

(73) Assignee: Mirowski Family Ventures, L.L.C., Washington, DC (US)

( * ) Notice: Subject to any disclaimer, the term of this patent is extended or adjusted under 35 U.S.C. 154(b) by 0 days.

(21) Appl. No.: 13/487,891

(22) Filed: Jun. 4, 2012

(65) Prior Publication Data

US 2012/0253418 A1    Oct. 4, 2012

Related U.S. Application Data

(60) Continuation of application No. 11/745,593, filed on May 8, 2007, now Pat. No. 8,249,725, which is a division of application No. 10/625,526, filed on Jul. 24, 2003, now Pat. No. 7,231,249.

(51) Int. Cl.
*A61N 1/362* (2006.01)

(52) U.S. Cl.
USPC ........ 607/148; 607/7; 607/9; 607/11; 607/17; 607/62; 607/66

(58) Field of Classification Search
USPC ........................ 607/7, 9, 11, 17, 62, 66, 148
See application file for complete search history.

(56) References Cited

U.S. PATENT DOCUMENTS

| | | | |
|---|---|---|---|
| 3,345,990 A | 10/1967 | Berkovits | |
| 3,431,912 A | 3/1969 | Keller, Jr. | |
| 3,433,228 A | 3/1969 | Keller, Jr. | |
| 3,595,242 A | 7/1971 | Berkovits | |
| 3,648,701 A | 3/1972 | Botts | |
| 3,747,604 A | 7/1973 | Berkovits | |
| 3,814,106 A | 6/1974 | Berkovits | |
| 3,903,897 A | 9/1975 | Woolons et al. | |
| 3,937,226 A | 2/1976 | Funke | |
| 4,052,991 A | 10/1977 | Zacouto | |

(Continued)

FOREIGN PATENT DOCUMENTS

| EP | 0017447 | 10/1980 |
|---|---|---|
| EP | 0039269 | 11/1981 |

(Continued)

OTHER PUBLICATIONS

Office Action issued Oct. 31, 2012 in European Application No. 09 158 987.9.

(Continued)

*Primary Examiner* — Christopher D Koharski
*Assistant Examiner* — Natasha Patel
(74) *Attorney, Agent, or Firm* — Oblon, Spivak, McClelland, Maier & Neustadt, L.L.P.

(57) ABSTRACT

Methods, apparatus, and systems are provided to stimulate multiple sites in a heart. A controller senses electrical activity associated with sinus rhythm of the heart. A signal generator is configured to generate an electrical signal for stimulating the heart. Based on the electrical signal, a distributor circuit then distributes the stimulating signals, such as pacing pulses, to a heart. The distributor circuit may vary the delay time between stimulating signals, inhibit a stimulating signal, trigger application of a stimulating signal, or vary the characteristics, such as the pulse width and amplitude, of a stimulating signal.

11 Claims, 9 Drawing Sheets

(56) References Cited

U.S. PATENT DOCUMENTS

| | | | |
|---|---|---|---|
| 4,057,067 A | 11/1977 | Lajos | |
| 4,088,140 A | 5/1978 | Rockland et al. | |
| 4,303,075 A | 12/1981 | Heilman et al. | |
| 4,312,355 A | 1/1982 | Funke | |
| 4,332,259 A | 6/1982 | McCorkle, Jr. | |
| 4,335,727 A | 6/1982 | McPherson | |
| 4,354,497 A | 10/1982 | Kahn | |
| 4,378,020 A | 3/1983 | Nappholz et al. | |
| 4,401,119 A | 8/1983 | Herpers | |
| 4,418,695 A | 12/1983 | Buffet | |
| 4,429,697 A | 2/1984 | Nappholz et al. | |
| 4,452,248 A | 6/1984 | Keller, Jr. | |
| 4,458,677 A | 7/1984 | McCorkle, Jr. | |
| 4,541,417 A | 9/1985 | Krikorian | |
| 4,548,203 A | 10/1985 | Tacker, Jr. et al. | |
| 4,554,922 A | 11/1985 | Prystowsky et al. | |
| 4,561,442 A | 12/1985 | Vollmann et al. | |
| 4,624,260 A | 11/1986 | Baker, Jr. et al. | |
| 4,628,934 A | 12/1986 | Pohndorf et al. | |
| 4,685,446 A | 8/1987 | Choy | |
| 4,705,043 A | 11/1987 | Imran | |
| 4,712,555 A | 12/1987 | Thornander et al. | |
| 4,727,877 A | 3/1988 | Kallok | |
| 4,774,950 A | 10/1988 | Cohen | |
| 4,790,317 A | 12/1988 | Davies | |
| 4,799,486 A | 1/1989 | DuFault | |
| 4,817,608 A | 4/1989 | Shapland et al. | |
| 4,827,932 A | 5/1989 | Ideker et al. | |
| 4,827,934 A | 5/1989 | Ekwall | |
| 4,830,006 A | 5/1989 | Haluska et al. | |
| 4,925,443 A | 5/1990 | Heilman et al. | |
| 4,928,688 A | 5/1990 | Mower | |
| 4,932,407 A | 6/1990 | Williams | |
| 4,967,749 A | 11/1990 | Cohen | |
| 4,974,588 A | 12/1990 | Smits | |
| 5,014,696 A | 5/1991 | Mehra | |
| 5,024,222 A | 6/1991 | Thacker | |
| 5,083,563 A | 1/1992 | Collins | |
| 5,099,838 A | 3/1992 | Bardy | |
| 5,111,811 A | 5/1992 | Smits | |
| 5,129,394 A | 7/1992 | Mehra | |
| 5,158,097 A | 10/1992 | Christlieb | |
| 5,213,098 A | 5/1993 | Bennett et al. | |
| 5,251,621 A | 10/1993 | Collins | |
| 5,312,440 A | 5/1994 | Hirschberg et al. | |
| 5,318,591 A * | 6/1994 | Causey et al. | 607/5 |
| 5,318,593 A | 6/1994 | Duggan | |
| 5,324,327 A | 6/1994 | Cohen | |
| 5,334,222 A | 8/1994 | Salo et al. | |
| 5,397,336 A | 3/1995 | Hirschberg et al. | |
| 5,545,204 A | 8/1996 | Cammilli et al. | |
| 5,556,420 A * | 9/1996 | Mortazavi et al. | 607/9 |
| 5,584,868 A | 12/1996 | Salo et al. | |
| 5,626,620 A | 5/1997 | Kieval et al. | |
| 5,797,970 A | 8/1998 | Pouvreau | |
| 5,800,465 A | 9/1998 | Thompson et al. | |
| 5,814,079 A | 9/1998 | Kieval | |
| 5,899,930 A | 5/1999 | Flynn et al. | |
| 5,902,324 A | 5/1999 | Thompson et al. | |
| 5,919,209 A | 7/1999 | Schouten | |
| 5,935,160 A | 8/1999 | Auricchio et al. | |
| 6,185,459 B1 | 2/2001 | Mehra et al. | |
| 6,298,268 B1 | 10/2001 | Ben-Haim et al. | |
| 6,317,631 B1 | 11/2001 | Ben-Haim et al. | |
| 6,324,425 B1 | 11/2001 | Blow et al. | |
| 6,330,476 B1 | 12/2001 | Ben-haim et al. | |
| 6,337,995 B1 | 1/2002 | Mower | |
| 6,463,324 B1 | 10/2002 | Ben-Haim et al. | |
| 6,549,806 B1 | 4/2003 | Kroll | |
| RE38,119 E | 5/2003 | Mower | |
| 6,587,720 B2 | 7/2003 | Hsu et al. | |
| 6,760,623 B2 | 7/2004 | Stahmann et al. | |
| 6,937,895 B1 | 8/2005 | Lu | |
| 7,894,915 B1 | 2/2011 | Chitre et al. | |
| 2003/0023280 A1 * | 1/2003 | Thompson | 607/9 |
| 2003/0074029 A1 | 4/2003 | Deno et al. | |
| 2003/0083710 A1 | 5/2003 | Ternes et al. | |
| 2003/0083711 A1 | 5/2003 | Yonce et al. | |
| 2005/0090865 A1 * | 4/2005 | Sun et al. | 607/2 |
| 2007/0162082 A1 | 7/2007 | Ternes et al. | |

FOREIGN PATENT DOCUMENTS

| | | |
|---|---|---|
| EP | 0 494 487 | 7/1992 |
| EP | 0 494487 | 1/1996 |
| EP | 0 726 082 | 8/1996 |
| EP | 0 813 889 A2 | 12/1997 |
| EP | 1 155 712 A2 | 11/2001 |
| EP | 1 249 254 | 10/2002 |
| GB | 2119255 | 7/1975 |
| GB | 1401247 | 11/1983 |
| WO | 82/03783 | 11/1982 |
| WO | 86/05698 | 10/1986 |
| WO | WO 02/053026 A2 | 7/2002 |

OTHER PUBLICATIONS

International Search Report, PCT/US2004/019107, Nov. 15, 2004.

Morton M. Mower, U.S. Appl. No. 10/214,474, "Method and Apparatus for Treating Hemodynamic Disfunction" filed Aug. 8, 2002, (Continuation Reissue Application of U.S. Patent No. 4,928,688).

Picture of Biventricular Pacer manufactured by American Optical Co., American Optical Corp., Research Division, Biventricular Pacer Device, 1975.

Aranda, et al., "A New Pacemaker for Simultaneous Biventricular Stimulation of the Human Heart," Clin. Res., vol. XXIV, No. 3, p. 206A (1976).

Badeer, "Relation of ECG to Mechanical Events," Cardiovascular Physiology, 1984, 6:57-58.

Bailon, et al., "Some Data for an Unanswered Question: Choosing the Ventricular Electrode Place," Pacing and Clinical Electrophysiology, vol. 8, No. 3, Part II, p. A-11 (1985).

Bakker et al., "Beneficial Effects of Biventricular Pacing in Congestive Heart Failure," PACE, 1994, Apr. 17 (4):820.

Bakker et al., "Biventricular Pacing in Congestive Heart Failure," Clinical Research, vol. 42, No. 2, Apr. 1994, p. 327A.

Bakker et al., "Biventricular Pacing Improves Functional Capacity in Patients with End-Stage Congestive Heart Failure," PACE, NASPE Abstracts 1995 (18):825.

Barold, et al., "First Reports of Electrical Multisite Ventricular Activation in Humans" PACE, Dec. 2000, (23):2117-2119.

Bashir, et al., "Combined Use of Transesophageal ECHO and Fluroscopy for the Placement of Left Ventricular Pacing Leads via the Coronary Sinus," PACE, Oct. 2003, (26):1951-1954.

Befeler, et al., "Programmed Simultaneous Biventricular Stimulation in Man, with Special Reference to its Use in the Evaluation of Intraventricular Reentry" Eur. J. of Cardiology, vol. 9, No. 5, pp. 369-378 (1979).

Benchimol et al., "Cardiac Hemodynamics During Stimulation of the Right Atrium, Right Ventricle, and Left Ventricle in Normal and Abnormal hearts," Circulation, vol. 33, Jun. 1966, pp. 933-944.

Benchimol, et al. "Contribution of Atrial Systole to the Cardiac Function at a Fixed and at a Variable Ventricular Rate," The American Journal of Cardiology, vol. 16, No. 1, Jul. 1965, pp. 11-21.

Blackburn et al., "Ventricular Pacing from the Coronary Sinus of a Patient with a Fontan Circulation" Br. Heart J., 1993, (70);578-579.

Bocchiardo et al., "Efficacy of Biventricular Sensing and Treatment of Ventricular Arrhythmias" PACE, vol. 23, 2000 Nov. 1989-1991.

Bourassa, "Hemodynamic Studies During Intermittent Left Bundle Branch Block," American Journal of Cardiiology, Dec. 1962, pp. 792-799.

Bove et al., "Ventricular Interdependence," Prog. Cardiovasc. Dis., Mar.-Apr. 1981 23(5):365-388.

Bracke et al., "Extraction of Pacemaker and Implantable Cardioverter Defibrallator Leads: Patient and Lead Characteristics in Relation to the Requirement of Extraction Tool," PACE, Jul. 2002, (25):1037-1040.

(56) References Cited

OTHER PUBLICATIONS

Broka et al., "Hemodynamic Effects of Atrio-Biventricular Pacing," Ann. Thoracic Surg., 1995, (60):1156.
Brownlee et al., "New functional Configurations for Adaptive Pacemakers," 28th ACEMB, New Orleans, Sep. 20-24, 1975, p. 84.
Brownlee et al., "Advances in Ventricular Synchronous Demand Cardiac Pacemakers," Med. Instrum., Mar.-Apr. 1978; 12(2):94-99.
Brownlee et al., "New Interference Sensing Demand Pacemaker functions," IEEE Transaction on Biomedical Engineering, May 1978, vol. BME 25, No. 3, pp. 264-269.
Castellanos et al., "Bipolar Coronary Sinus Lead for Left Atrial and Left Ventricular Recording," American Heart Journal, 1971, vol. 81, No. 6, pp. 832-836.
Castellanos et al., "Measurement of Conduction Times with Catheter Electrodes During Pacing from Different Ventricular Sites", British Heart Journal, 1975, (37):242-248.
Castellanos et al., "Unusual QRS Complexes Produced by Pacemaker Stimuli," American Heart Journal, Jun. 1969, vol. 77, No. 6, pp. 732-742.
Cazeau et al., "Four Chamber Pacing in Dilated Cardiomyopathy," PACE, Nov. 1994, Part II, vol. 17, 1974-1979.
Cazeau et al., Multisite Pacing for End-Stage Heart Failure, PACE, Nov. 1996, (19):1748-1757.
Cazeau et al., "Echocardiographic Modeling of Cardiac Dyssynchorny Before and During Multisite Stimulation: A Prospective Study," PACE, Jan. 2003, Part II, (26):137-143.
Chamorro et al., "Ejection VAVE; EF and Phase Histogram to Evaluate a Correct Programation of AV Delay in DDD Pacemakers," European Journal of Nuclear Medicine, vol. 8, No. 5, pp. A 36 (1983).
Cohen et al., "Hemodynamic Responses to Rapid Pacing: A Model for Tachycardia Differentiation," PACE, Nov. 1988, (11):1522-1528.
Cordis Articor Manual, Implantable P-Wave Synchronized Cardiac Pacers, Model 145, 149-Rev. 3A, Oct. 1973, pp. I-1 to VIII-1.
Curtiss et al., "Electrocardiographically Discrete Right and Left Ventricular QRS Complexes: A Case Report," J. Electrocardiol., Apr. 1987; 20(2):162-168.
D'Aiotolo et al., "Tratamiento De Las Arritmias Cardiacas," Buenos Aires (1968) (in spanish). pp. 1-112.
David et al., "Atrial Alternans: Experimental Echocardiographic and Hemodynamic Demonstration During Programmed Pacing," Am. J. of Cardiology, Sep. 1981, vol. 48, pp. 468-472.
Dawson et al., "Regional Left Ventricular Wall Motion in Pacing induced Angina," Br. Heart J., 1988, 59(3):309-318.
Dawson et al., "Left Ventricular Filling and Early Diastolic Function at Rest and During Angina in patients with Coronary Artery Disease," Br. Heart J. 1989, 61(3):248-257.
De Teresa et al., "An Even more Physiological Pacing: Changing the Sequence of Ventricular Activation," Cardiac Pacing: Proceedings of the VIIth World Symposium on Cardiac Pacing, Vienna, May 1-5, 1983, Steinkopff Verlag Darmstadt 1983, pp. 395-400.
De Teresa et al., "Haemodynamics of Ventricular Depolarization Sequence During Permanent Cardiac Pacing," Cardio Stimolazione, vol. 2, No. 3, p. 225 (1984).
De Teresa et al., "Haemodynamics of Ventricular Depolarization Sequence During Permanent Cardiac Pacing," Progress in Clinical Pacing, Proceedings Ed. by Santini et al., pp. 888-894, Rome (1984).
Dreifus et al., "Use of atrial and bifocal cardiac pacemakers for treating resistant dysrhythmias," Eur. J. Cardiol., Dec. 1975; 3(4):257-266.
Dreifus et al., "Effect of multiple simultaneous activation sites (biventricular pacing) on ventricular depolarization and ventricular arrhythmias," Cardiac Pacing, Proceedings of the Vth International Symposium, Tokyo, Mar. 1976, pp. 33-39.
Duck et al., "Vorhofsynchrone Ventrikelstimulation mit verkurzter a.v. Verzogerungszeit als Therapieprinzip der hypertrophischen obstruktiven Kardiomyopathie" "[Atrial Synchronous Ventricular Stimulation With Reduced a.v. Delay Time as a Therapeutic Principle in Hypertrophic Obstructive Cardiomyopathy]," Z. Gesamte Inn. Med., Sep. 15, 1984 (39):18 437-447. (German with English Language Abstract Attached).

Fei et al., "Effects of Multisite Ventricular Pacing on Cardiac Function in Normal Dogs and Dogs with Heart Failure," Journal of Cardiovascular Electrophysiology, Jul. 1999 10(7):935-946.
Finney, Jr., "Hemodynamic alterations in Left Ventricular Function Consequent to Ventricular Pacing," American J. Physiology, 1965, 208(2):275-282.
Foster et al., "Acute Hemodynamic Effects of Atrio-Biventricular Pacing in Humans," Annals of Thoracic Surg., 1995-55:294-300.
Funke, "[Optimized Sequential Pacing of Atrium and Ventricle—A New Therapeutic Concept in the Treatment of Bradycardial Dysrhythmias]," Herz/Kreisl., Oct. 1978; 10(10):479-483 (German with English-Language Abstract and English Translation Attached).
Furuta et al., "[Assessment of interaction between the left and right ventricles using pressure-volume loops in various heart diseases]," J. Cardiol., Jun. 1988; 18(2):477-491. (Japanese with English Abstract and Figure Captions).
Gasparini et al., on behalf of the Italian InSync ICD Registry Investigators, "Cardiac Resynchronization and Implantable Cardioverter Defibrillator Therapy: Preliminary Results from the InSync Implantable Cardioverter Defibrillator Italian Registry," PACE, Jan. 2003 26(1):2, 148-151.
Gasparini et al., "Beneficial Effects of Biventricular Pacing in Patients with a 'Narrow' QRS," PACE, Jan. 2003, 26(1):2, 169-174.
Gibson et al., "Effect of Changes in Ventricular Activation on Cardiac Haemodynamics in Man: Comparison of Right Ventricular, Left Ventricular, and Simultaneous Pacing of Both Ventricles," Br. Heart J., May 1971; 33(3):397-400.
Gilmore et al., "Synchronicity of Ventricular Contraction: Observations Comparing Haemodynamic Effects of Atrial and Ventricular Pacing" Br. Heart J., May 1963; 25:299-307.
Greatbatch, "The Making of the Pacemaker: Celebrating Lifesaving Invention," Prometheus Books, 2000, pp. 1-260, particularly pp. 14-19.
Gomez-Doblas et al., "Ventricular Geometry and Heart Failure", Rev. Esp. Cardiol., Jan. 1999, 52(1):47-52. Review. (Spanish with English Abstract0.
Grover et al., "Endocardial Pacing Site Affects Left Ventricular End-Diastolic Volumn and Performance in the Intact Anesthetized Dog", Cirulartion Research, Jul. 1983, 53(1):72-85.
Hass et al., "Pacemaker-Induced Cardiovascular Failure," Am. J. of Cardiology, vol. 33, pp. 295-299 (Feb. 1974).
Hauser et al., "Performance of Pacemaker and Implantable Cardioverter Defibrillator Pulse Generators and Leads: Results from the Multicenter Registry," The XIIth World Congress on Cardiac Pacing & Electrophysiology, Hong Kong, Feb. 19-22, 2003, pp. 173-179.
Hayes et al., "Cardiac Pacing: How it Started, Where We Are, Where We Are Going," PACE, May 2004, 27:693-704.
Hochleitner et al., "Usefulness of Physiologic dual-chamber Pacing in Drug-Resistant Idiopathic Dilated Cardiomyopathy", American Journal of Cardiology, Jul. 15, 1990, (66):198-202.
Hughes et al., "Effect of Stimulation Site on Ventricular Threshold in Dogs with Heart Block." American Heart Journal, Jan. 1975, 89(1):68-73.
Hughes et al., "Two to Three Years of Failure-Free Testing of a Rechargeable Pacemaker in Experimental Complete Heart Block," Circulation, Aug. 1976, 54(2):263-266.
Hughes et al., "The Effects of Electrode Position on the Detection of the Transvenous Cardiac Electrogram", PACE, 1980, 3(6):651-655.
Hunt et al., "Long-term Electrode Catheter Pacing from Coronary Sinus", Medical Memoranda, British Medical Journal, Nov. 23, 1968, pp. 495-496.
Janosik et al., "The Hemodynamic Benefit of Differential Atrioventricular Delay Intervals for Sensed and Paced Atrial Events During Physiologic Pacing", J. Am. Coll. Cardiol., Aug. 1989, 14(2):499-507.
Jeffrey, Excerpts from *Machines in Our Hearts*, 2001, The John Hopkins University Press, Chapter 2, pp. 36-39, 65-66, 90-100, 118-120, 170-171 and 236-237.

(56) References Cited

OTHER PUBLICATIONS

Jimenez-Navarro et al., Correspondence to the Editor about "Left Ventricular Assist Device", N. Engl. J. Med., Mar. 28, 2002, 346(13):1023-1025; author reply 1023-1025.

Karlof, Ingvar, "Haemodynamic Effect of Atrial Triggered Versus Fixed Rate Pacing at Rest and During Exercise in Complete Heart Blook", Acta. Med. Scand., 197(3):195-206, Mar. 1975.

Kawamura et al., "[83. Experimental Study of RV-LV Simultaneous Pacing as More Physiological Pacing]," Idem Job No. 0412-137, 1982, pp. 285-286. (Japanese with English Translation).

Kennergren, et al., "Cardiac Lead Extraction with a Novel Locking Stylet," Journal of Interventional Cardiac Electrophysiology, 2000, V. 4, pp. 591-593.

Kerr et al., "Transvenous Atrial Pacing Following Amputation of the Atrial Appendage at Open Heart Surgery," PACE, Jul.-Aug. 1985, (8):497-501.

Kerr et al., "Atrial Pacing: Efficacy and Safety,"PACE, Jul. 1989, 12(1):1049-1054.

Klug et al., "Pacemaker Lead Extraction with the Needle's Eye Snare for Countertraction via a Femoral Approach," PACE, Jul. 2002, 25(7):1023-1028.

Lattuca et al., "Bi-Ventricular Pacing to Improve Cardiac Hemodynamics," Clinical Research, Oct. 1990, 38(3):882A.

Lima et al., "Incomplete Filling and Incorrdinate Contraction as Mechanisms of Hypotension during Ventricular Tachycardia in Man," Circulation, vol. 68, No. 5, pp. 928-937 (1983).

Lister et al., Effect of Pacemaker Site on Cardiac Output and Ventricular Activation in Dogs with Complete Heart Block,: Am. J. of Cardiology, vol. 14, pp. 494, 496, 500 (1964).

Magder et al., "Effect of Negative Pleural Pressure on Left Ventricular Hemodynamics," Am. J. of Cardiology, Sep. 1, 1983, 52(5), pp. 588-593 (Abstract Only).

Mann et al., "Importance of Pacing Site in Entrainment of Ventricular Tachycardia," J. Am. College of Cardiology, vol. 5, No. 3, pp. 781-787 (1985).

Marchlinski et al., "Atrial and Ventricular Burst Pacing from a Coronary Sinus Catheter: Relation to Position of Radiofrequency Transmitter," PACE, May-Jun. 1985, 8(1), 399-401.

McIntosh et al., "The Hemodynamic Consequences of Arrhythmias," Prog. Cardiovasc. Dis., 8(4):330-363 (1966).

Medtech Insight, "Hot Topics in Heart Failure," Jun./Jul. 2004, cover page and pp. 190-200.

Mehta, et al., "Cardiology's 10 Greatest Discoveries of the $20^{th}$ Century," Texas Heart Institute Journal, 2002, 9(3):164-171.

Mercando et al., "Measurement of Differences in Timing and Sequence Between Two Ventricular Electrodes as a Means of Tachycardia Differentiation," PACE, Nov.-Dec. 1986, 9(11):1069-1078.

Mirowski et al., "A Chronically Implanted System for Automatic Defibrillation in Active Conscious Dogs," Circulation, Jul. 1978; 58(1):90-94.

Mirowski et al., "Clinical Experience with the Implantable Cardioverter-Defibrillator," Annals of the New York Academy of Sciences, 1984, 427:297-306.

Mirowski et al., "Clinical Experience with the Automatic Implantable Defibrillator," Arch. M. Com., 1985, pp. 39-42.

Mirowski, et al., "The Automatic Implantable Cardioverter-Defibrillator," PACE, May-Jun. 1984, Part II, 7:534-540.

Mirowski et al., "Use of the Automatic Implantable Cardioverter-Defibrillator in the Treatment of Malignant Ventricular Tachyarrhythmias," Herz, 1984, 9(2):83-89.

Mirowski et al., "Clinical Performance of the Implantable Cardioverter-Defibrillator," PACE, Nov.-Dec. 1984, Part II, 7:1345-1350.

Molhoek et al., "QRS Duration and Shortening to Predict Clinical Response to Cardiac Resynchronization Therapy in Patients with End-Stage Heart Failure," PACE, Mar. 2004, 27:308-313.

Moore et al., "Electrophysiological Studies on Pacing Techniques to Prevent Ventricular Fibrillation," Chapter 22 from Nonpharmacological Therapy of Tachyarrhythmias, Futura Pub. Co., 1987, pp. 345-358.

Mortensen et al., "Sequential Biventricular Pacing: Evaluation of Safety and Efficacy," PACE, Mar. 2004, 27:339-345.

Moss, "Long-Term Pervenous Atrial Pacing From the Proximal Portion of the Coronary Vein," JAMA, Jul. 28, 1969, 209(4):543-545.

Moulopoulos, et al., "Effect of Site and Intensity of Pacing on Left Ventricular Performance," J. Electocardiology, 16(4):409-415 (1983).

Mower et al., "Unusual Patterns of Conduction Produced by Pacemaker Stimuli," Am. Heart J., Jul. 1967; 74(1):24-28.

Mower et al., "Automatic Implantable Cardioverter-Defibrillator Structural Characteristics," PACE, Nov.-Dec. 1984, 7(No. 6, Pt 2):1331-1337.

Navarro-Lopez et al., "Guideline 8. Criteria for Hospitalization," Rev. Esp. Cardiol, 1997, 50(Supp.1):47-48. (Spanish with English Abstract).

Navarro-Lopez et al., "Guideline 1. Diagnosis of Heart Failure and Ventricular Dysfunction," Rev. Esp. Cardiol., 1997, 50(Supp.1);3-8 (Spanish with English Abstract).

Navarro-Lopez et al. "Guideline 4. Management of Congestive Heart Failure," Rev. Esp. Cardiol., 1997, 50(Supp.1):27-31. (Spanish with English Abstract).

Navarro-Lopez et al., "Guidelines for the Diagnosis and Management of Heart Failure and Cardiogenic Shock," Rev. Esp. Cardiol., 1999, 52(Supp. 2):1-54. (Spanish with English Abstract).

Ong et al., "Cephalic Vein Guide Wire Technique for Implantation of Permanent Pacemakers," American Heart Journal, Oct. 1987, 4(1):753-756.

Park et al., "Effect of Alteration of Left Ventricular Activation Sequence on the Left Ventricular End-Systolic Pressure-Volume Relation in Closed-Chest Dogs," Circulation Research, vol. 57, No. 5, Nov. 1985, pp. 706-717.

Patel et al., Letters to the Editor: "Coronary Sinus Pacing," Circulation, vol. 58, No. 1, Jul. 1978, pp. 187-189.

Peschar et al., "Left Ventricular Septal and Apex Pacing for Optimal Pump Function in Canine Hearts," Journal of the American College of Cardiology, 2003, 41(7):1218-1226.

Platia et al., "Management of the Prolonged QT Syndrome and Recurrent Ventricular Fibrillation with an Implantable Automatic Cardioverter-Defibrillator," Clinical Cardiology, 1985-8:490-493.

Platia et al., "Sensitivity of Various Extrastimuls Techniques in Patients with Serious Ventricular Arrhythmias," American Heart Journal, Oct. 1983, 106(4):698-703.

Platia et al., "Treatment of Malignant Ventricular Arrhythmias with Endocardial Resection and Implantation of the Automatic Cardioverter-Defibrillator," The New England Journal of Medicine, Jan. 1986, 314(4):213-216.

Prinzen et al., "Relation Between the Pacing Induced Sequence of Activation and Left Ventricular Pump Function in Animals," PACE, Apr. 2002, Part 1, 25(4):484-498.

Reid et al., "Clinical Evaluation of the Internal Automatic Cardioverter-Defibrillator in Survivors of Sudden Cardiac Death," Am. J. Cardiol., Jun. 1983; 51:1608-1609.

Ritter, "Editorial," PACE, Jan. 2003, Part II, 26:136.

Rogel et al., "The Universal Pacer: A Synchronized-Demand Pacemaker," J. Thorac. Cardiovasc. Surg., Mar. 1971; 61(3):466-471.

Rosenheck et al., "Noninstrumental Pacemaker and Defibrillator Lead Removal: The Importance of the Rotation Forces," PACE, vol. 25, No. 7 Jul. 2002, pp. 1029-1036.

Rosenqvist et al., "Relative Importance of Activation Sequence Compared to Atrioventricular Synchrony in Left Ventricular Function," Am. J. of Cardiology, vol. 67, Jan. 15, 1991, pp. 148-156.

Samet et al., "Electrical Activation and Mechanical Asynchronism in Cardiac Cycle of the Dog," Circulation Research, vol. VII, Mar. 1959, pp. 228-233.

(56) References Cited

OTHER PUBLICATIONS

Santamore et al., "A Theoretical and Experimental Model of Ventricular Interdependence," Basic Res. Cardiol., Sep.-Oct. 1986; 81(5):529-538.
Schlant et al., "Modification of the Law of the Heart: Influence of Early Contracting Areas (P)," Supp. to Circulation, vols. XXIX and XXX, Oct. 1964, pp. 153-154.
Shefer et al., "Left Ventricular Function During Physiological Cardiac Pacing: Relation to Rate, Pacing Mode, and Underlying Myocardial Disease," PACE, vol. 10 Mar.-Apr. 1987, pp. 315-325.
Silva et al., "Biventricular Stimulation: A More Physiologic Pacing," 4th European Symposium on Cardiac Pacing, May 28-31, 1989, Abstract 339, pp. 148.
Silva, "Influencia de la Localizacion de la Estimulacion Electrica Ventricular Sobre la Eficiencia Cardiaca. Estudio Experimental Y Clinico," Tesis Doctoral para la Universidad Autonoma De Madrid Facultad de Medicina (1987), pp. 1-150 (Doctoral Thesis, in Spanish).
Silva et al., "Biventricular Stimulation: An Approach to Physiologic Cardiac Stimulation," International Congress of Cardiology, Abstracts, pp. 132 (Nov. 1988).
Sodi-Pollares, et al., "General Considerations about the Activation Process of the Heart," Deductive and Polyparametric Electrocardiography, 1970, pp. 30-41.
Takeshita et al., "Effect of Intermittent Left Bundle Branch Block on Left Ventricular Performance," Am. J. of Medicine, vol. 56, Feb. 1974, pp. 251-255.
Tsagaris et al., "Species Variability in Hemodynamic Response to Paired-Pulse Stimulation," Am. J. of Physiology, Jun. 1969, 216(6):1409-1417.
Tyers, "Comparison of the Effect on Cardiac Function of Single-Site and Simultaneous Multiple-Site Ventricular Stimulation after A-V Block," J. Thoracic and Cardiovas. Sur., vol. 59, No. 2, pp. 211-217 (1970).
Tyers, "Maximum Cardiac Performance after Complete Heart Block," Surgical Forum, vol. XVIII, American College of Surgeons, 1967, pp. 132-133.
Tyers, "Optimal Electrode Implantation Site for Asynchronous Dipolar Cardiac Pacing," Annals of Surgery, Feb. 1968, 167(2):168-179.
Tyers et al., "An Integrated Program for Safe Permanent Internal Cardiac Pacing," The Journal of Cardiovascular Surgery, 11th World Congress of International Cardiovascular Society, Barcelona, Sep. 27-29, 1973, Special Issue, pp. 163-166.
Tyers et al., "Effect of Site of Synchronous Unipolar Ventricular Stimulation and Volume Loading on Cardiac Function," J. Surg. Res., Oct. 1973; 15(4):271-284.
Tyers et al., "Comparative Studies of 'state of the art' and Presently Used Clinical Cardiac Pacemaker Electrodes," Journal of Thoracic and Cardiovascular Surgery, St. Louis, vol. 67, No. 6, Jun. 1974, pp. 849-856.
Tyers et al., "The Advantages of Transthoracic Placement of Permanent Cardiac Pacemaker Electrodes," Journal of Thoracic and Cardiovascular Surgery, Jan. 1975, 69(1):8-14.
Tyers et al., "The unfulfilled Promise of Demand Pacing," Journal of Thoracic and Cardiovascular Surgery, Nov. 1976, 72(5):813-814.
Tyers et al., "Improved R-Wave Detection with Intramyocardial Elecrodes," 30th ACEMB, Los Angeles Hilton, Los Angeles, CA, Nov. 5-9, 1977, p. 268.
Tyers et al., "R-Wave Detection for Demand Pacing—The Superiority of Intramyocardial Over Endocardial Electrodes," J. Surg. Res., Apr. 1978, 24(4):316-320.
Tyers et al., "Myocardial Stimulation Impedance: The Effects of Electrode, Physiological, and Stimulus Variables," Annals of Thoracic Surgery, 27(1):63-69 (1979).
Tyers et al., "Multiprogrammable Pacemakers," Canadian Journal of Surgery, 1981, 24(3):252-256.
Tyers et al., "Current Status and Future of Programmable Pacing," Vogel, J.H.K. (Ed.). Cardiovascular Medicine, vol. 1., Raven Press: New York, N.Y., (1982), pp. 355-362.
Tyers et al., "Current Status of Sensor-Modulated Rate-Adaptive Cardiac Pacing," Journal of the American College of Cardiology, 1990 15(2):412-418.
Tyers et al., "Medical Device Review in Canada," PACE, Mar. 1995, 18(3):472-473.
Tyers et al. "Coradial Bipolar Lead Implant and Follow-Up Experience," Poster Presentation at the North American Society for Pacing and Electrophysiology (NASPE), 17th Annual Scientific Sessions, Seattle, WA, May 15-18, 1996, 4 pages.
Tyers et al., "Removal of Permanent Endocardial Pacing Leads (1981-1997)," Heartweb, vol. 4, No. 4, Feb. 1999, (Article No. 9920003), pp. 1-8.
Tyers et al., "Bipolar Leads for Use with Permanently Implantable Cardiac Pacing Systems: A review of Limitations of Traditional and Coaxial Configurations and the Development and Testing of New Conductor, Insulation, and Elecrrode Designs," J. Invest. Surg., 1997, 10(1):1-15.
Tyers et al., "Similar Indications but Different Methods: Should there be a Consensus on Optimal Lead Extraction Techniques?", PACE, Jul. 2002, 25(7):1019-1022.
Tyers et al., "Bifocal/Biatrial Pacing in Clinical Practice," World Congress on Cardiac Pacing & Electrophysiology, Hong Kong, Feb. 19-22, 2003, pp. 715-717.
Tyers et al., "Coronary Sinus Lead Extraction," The XIIth World Congress on Cardiac Pacing & Electrophysiology, Hong Kong, Feb. 19-22, 2003, pp. 741-743.
Tyers et al., "Surgical Complications of Pacemaker Implant," The XIIth World congress on Cardiac Pacing & Electrophysiology, Hong Kong, Feb. 19-22, 2003, pp. 745-760.
Waldo et al., "Ventricular Paired Pacing to Control Rapid Ventricular Heart Rate Following Open Heart Surgery," Circulation, Jan. 1976, 53(1):176-181.
Walsh et al., "Differentiation of Sinus Rhythms for Supraventricular Tachydysrhythmias by Activation Sequence and Timing," PACE Dec. 1990; 13(12 Pt. 2):1972-9 (Abstract Only).
Watkins, Jr. et al., "Surgical Techniques for Implanting the Automatic Implantable Defibrillator," PACE, Nov.-Dec. 1984, Part II, 7:1357-1362.
Watkins et al., "The Treatment of Malignant Ventricular Arrhythmias with Combined Endocardial Resection and Implantation of the Automatic Defibrillator: Preliminary Report," The Annals of Thoracic Surgery, Jan. 1984, 37(1):60-64.
Watkins et al., "Malignant Ventricular Arrhythmias," The Annals of Thoracic Surgery, Jan. 1984, 37(1):65-66.
Watkins et al., "Automatic Implantable Defibrillator," The Journal of Thoracic and Cardiovascular Surgery, Sep. 1983, 86(3):382-387.
Watkins et al., "Automatic Defibrillation in Man: Is it Feasible?" The American Journal of Surgery, Jun. 1983, 145:752-755.
Waxman et al., "Ventricular Pacing from the Middle Cardiac Vein Mimicking Supraventricular Morphology" PACE, vol. 2, Mar.-Apr. 1979, pp. 203-207.
William-Olsson et al., "The Effect of Pacemaker Electrode Site on Cardiac Output," J. Thoracic and Cardiovas. Surg., vol. 45, No. 5, pp. 618-621 (1963).
Wish et al., "Optimal Left Atrioventricular Sequence in Dual Chamber Pacing-Limitations of Programmed A-V Interval," JACC, vol. 3, No. 7, Feb. 1984, p. 507 (Abstract).
Witte et al., "Transvenous Atrial Synchronized Pacing," Advances in Pacemaker Technology, Springer-Verlag Pub.,1975, pp. 99-120.
Yoshimori, "An Experimental Study on the Site for Ventricular Pacing of a Dog Heart with Special Reference to Biventricular Pacing," Nippon Ika Daigaku Zasshi, vol. 54, No. 3 (1987), pp. 267-276. (Japanese with English-Language Abstract and English Translation Attached).
Zile et al., "Right Ventricular Pacing Reduces the Rate of Left Ventricular Relaxation and Filing," J. Am. Coll. Cardiol., vol. 10, No. 3, pp. 702-709 (1987).
Zipes et al., "Electrophysiologic Studies on Ventricular Fibrillation," Cardiac Electrophysiology and Arrhythmias, Gruni and Stratton, Pub., 1985, pp. 317-320.

(56) References Cited

OTHER PUBLICATIONS

Diotallevi et al., "Rescuing Failed Biventricular Implants using Right Ventricular Bifocal Pacing to Assure Cardiac Resynchronization Benefits to Heart Failure Patients," Heart Rhythm, vol. 3, No. 5, May Supplement 2006, Abstract No. AB48-2.
Leclercq et al., "Triple site Ventricular Pacing for Optimizing Ventricular Resynchronization: Design of the Trip-HF Study; Technical Feasibility," Heart Rhythm, vol. 3, No. 5, May Supplement 2006, Abstract No. AB48-3.
Niazi et al., "Dual-Site Left Ventricular Stimulation Provides Better Resynchronization Response than Conventional Biventricular Stimulation," Hear Rhythm, vol. 3, No. 5, May Supplement 2006, Abstract No. AB42-6.
Yoshida et al., "Tripolar-Ventricular Pacing Improves Both Systolic and Diastolic Left Ventricular Function in Patients with End-Stage Hear Failure," Heart Rhythm, vol. 3, No. 5, May Supplement 2006, Abstract No. P6-96.
Aranda et al., "A New Pacemaker for Simultaneous Biventricular Stimulation of the Human Heart," Clin. Res., vol. XXIV, No. 3, p. 206A (1976).
D'Aiutolo, R. and Posse, R, Tratamiento de Las Arritmias Cardiacas, Buenos Aires 1968 and English-Language translation of Chapter 10.
Morton M. Mower, U.S. Appl. No. 10/214,474, entitled "Method and Apparatus for Treating Hemodynamic Disfunction," filed Aug. 8, 2002 (Continuation Reissue Application of U.S. Patent No. 4,928,688).
Silva, "Influencia de la Localizacion de la Estimulacion Electrica Ventricular Sobre 1a Eficiencia Cardiaca. Estudio Experimental Y Clinico," ["Influence of the Location of the Location of Ventricular Electrical Stimulation on Cardiac Efficiency"], Tesis Doctoral para la Universidad Autonoma De Madrid Facultad de Medicina (Dated 1987) (Spanish with English-Language Translation Attached).
European Office Action, mailed Jul. 17, 2006, in corresponding European Application No. 04755341.7.
Invitation pursuant to Rule 62a(1) EPC and Rule 63(1) EPC issued Mar. 9, 2011, in European Patent Application No. 09 158987.9-2213.
Communication from European Patent Office issued Nov. 7, 2011 in Application No. 09158987.9.
Extended Search Report issued Oct. 5, 2011 in Europe Application No. 09158987.9.
Befeler, B, et al., "Cardiovascular Dynamics During Coronary Sinus, Right Atrial, and Right Ventricular Pacing," Am. Heart J., vol. 81, No. 3, Mar. 1971, pp. 372-380.
Benditt, DG et al., "Sensor-Triggered Rate-Variable Cardiac Pacing: Current Technologies and Clinical Implications," Annals of Internal Med., vol. 107, No. 5, Nov. 1987, pp. 714-724.
Berkovits, B, et al., "Bifocal Demand Pacing," Singapore Med. J., vol. 14, No. 3, Sep. 1973, pp. 316-319.
Berkovits, B, "Demand Pacing," Annals of New York Academy of Sciences, vol. 167, Art. 2, Oct. 1969, pp. 891-895.
Berkovits, B, et al. "Future Generation Pacemakers," Pacemaker Therapy, L. Dreifus ed., 1983, pp. 265-276.
Blanc JJ. et al.,"Recurrent Supraventricular Tachycardia: The Efficacy of a Radio Frequency System Inserted into the Coronary Sinus," Archives des Maladies du Coeur et des Vaisseaux, 1978, 71:687-90. b.
Blanc JJ, et al., "Evaluation of Different Ventricular Pacing Sites in Patients with Severe Heart Failure: Results of an Acute Hemodynamic Study," Circulation, vol. 96, No. 10, Nov. 1997, pp. 3273-3277.
Blanc JJ, et al., "A Method for Permanent Transvenous Left Ventricular Pacing," PACE, vol. 21, Nov. 1998, pp. 2021-2024.
Bognolo, DA, "Recent Advances in Permanent Pacemaker Implantation Techniques," Modern Cardiac Pacing, Barold SS, ed., Futura Publishing Co., 1985, pp. 199-229.
Bristow MR, et al., "Cardiac-Resynchronization Therapy With or Without an Implantable Defibrillator in Advanced Chronic Heart Failure," N. Engl. J. Med., vol. 350, 2004, 2140-50.
Burkoff, D, et al., "Influence of Pacing Site on Canine left Ventricular Contraction," Am. J. Physiol. (Heart Circ. Physiol.), 1986:20:H428-H435.
Castellanos, A. et al., "Atrial Demand and AV Sequential Pacemakers," Pacemaker Therapy, L. Dreifus, ed., 1983, pp. 149-164.
Castellanos, A. et al., "Cardiac Pacemakers," Cardiac Surgery 2, vol. 3, No. 2, D. Harken, ed., 1971, pp. 32-44.
Castellanos, A, et al., "Effects of Pacemaker Impulses on Latent Arrhythmias Produced by Intramyocardial Chemical Stimulation," Cardiologia, vol. 51, No. 6, 1967, pp. 340-348.
Castellanos, A, et al., "An Electrical Digitalis Tolerance Test," Am. J. of Medical Sciences, Nov. 1967, pp. 159-168.
Castellanos, A, et al., "The Electrocardiogram and Vectorcardiogram of Ectopic Ventricular Beats," Acta Cardiologica, vol. 28, No. 6, 1973, pp. 562-575.
Castellanos, A. et al., "Electronic Pacemaker Models of Parasystole: With Special Reference to Artificial Intermittent Parasystole with Phase 3 and Phase 4 Protection and to Parasystolic Modulation," PACE, vol. 5, No. 4, Jul. 1982, pp. 537-545.
Castellanos, A, et al., "Evaluacion Clinica De Los Marcapasos Implantados," Boletin de la Associacion Medica de Puerto Rico, vol. 73, No. 12, Dec. 1981, pp. 644-653.
Castellanos, A. et al., "His Bundle Recordings in Atrioventricular Nodal Alternating Wenckebach Periods Ending in 5:1 Atrioventricular Block Coexisting with Paroxysmal Atrioventricular Nodal Block," CHEST, vol. 74, No. 3, Sep. 1978, pp. 274-279.
Castellanos, A. et al "Implantable Demand Pacemaker," Brit. Heart J., vol. 30, 1968, pp. 29-33.
Castellanos, A, et al., "Implantable Pacemakers for Cardiac Tachyarrhythmias," Cardiac Arrythmias: Mechanisms and Management, A. Castellanos, ed., 1980, pp. 159-173.
Castellanos, A, et al., "A New Instrument for Automatic Monitoring and Tape Recording in Infants and Children," Boletin de la Associacion Medica de Puerto Rico, vol. 58, No. 7, Jul. 1966, pp. 355-359.
Castellanos, A., et al., "Pacemaker-Induced Cardiac Rhythm Disturbances," Annals of New York Academy of Sciences, vol. 167, No. 2, Oct. 1969, pp. 903-910.
Castellanos, A., et al., "Pacemaker Vectorcardiography," Am. Heart J., vol. 75, No. 1, Jan. 1968, pp. 6-18.
Castellanos, A, et al., "Pacing in Acute Myocardial Infarction: A Programmed Introduction," CHEST, vol. 58, No. 2, Aug. 1970, pp. 152-163.
Castellanos, A, et al., "Preliminary Studies with an Implantable Multimodal A-V Pacemaker for Reciprocating Atrioventricular Tachycardias," PACE, vol. 3, No. 3, May 1980, pp. 257-265.
Castellanos, A, et al., "Repetitive Firing Occurring During Synchronized Electrical Stimulation of the Heart," J. of Thoracic Cardiovascular Surgery, vol. 51, No. 3, Mar. 1966, pp. 334-340.
Castellanos, A, et al., "Sextapolar Catheter Elecrode for Temporary Sequential Atrioventricular Pacing," Cardiovascular Research, vol. 8, No. 5, Sep. 1974, pp. 712-714.
Castellanos, A, et al., "Significance of Multiple Responses Produced by Electrical Depolarization of the Heart," Acta Cardiologica, vol. 21, No. 2, 1966, pp. 157-166.
Castellanos, A. et al., "Simultaneous Biventricular Stimulation for Ventricular Arrhythmias," Am. J. Cardiol., vol. 88, Nov. 15, 2001, pp. 1217-1218.
Castellanos, A. et al., "A Study of Arrival of Excitation at Selected Ventricular Sites During Human Bundle Branch Block Using Close Bipolar Catheter Electrodes," CHEST, vol. 63, No. 2, Feb. 1973, pp. 208-213.
Castellanos, A. et al., "St-qR Pattern: New Sign for Diagnosis of Anterior Myocardial Infarction During Right Ventricular Pacing," Br. Heart J. vol. 35, Oct. 1973, pp. 1161-1165.
Castellanos, A. et al., "The Use of the Demand Pacemaker in Auriculo-Ventricular Conduction Disturbances," J. of Cardiovascular Surgery, vol. 7, No. 2, Mar.-Apr. 1966, pp. 92-96.
Castellanos, A. et al., "Ventricular-Triggered Pacemaker Arrhythmias," Brit. Heart J., vol. 31, 1969, pp. 546-552.

(56) References Cited

OTHER PUBLICATIONS

Castellanos, A. et al., "The Wedensky Effect in the Human Heart," Brit. Heart J., vol. 28, 1966, pp. 276-283.
Castillo, C, et al., "Bifocal Demand Pacing," CHEST, vol. 59, No. 4, Apr. 1971, pp. 360-364.
Cazeau S, et al., "Effects of Multisite Biventricular Pacing in Patients With Heart Failure and Intraventricular Conduction Delay," N. Engl. J. Med., vol. 344, 2001, pp. 873-880.
Chamorro, JL, et al., "Quantification of Experimental Myocardial Infarction with 99TcGlucogeptonate," European Journal of Nuclear Medicine, vol. 8, No. 5, 1983, Abstract P104.
De Teresa, E., Grandes Temas de la Medicina: Marcapasos, Nueva Lente, Madrid 1987.
Dreifus, L, et al., "Effects of AV Sequential Versus Asynchronous AV Pacing on Pulmonary hemodynamics," PACE, vol. 9, No. 2, Mar.-Apr. 1986, pp. 171-177.
Ellenbogen KA, et al., Clinical Cardiac Pacing and Defibrillation, $2^{nd}$ Edition, Philadelphia, W.B. Saunders Co., 2000.
Elmqvist, R, et al., "An Implantable Pacemaker for the Heart," Medical Electronics: Proceedings of the Second International Conference on Medical Electronics, Smyth, CN, ed., Jun. 1959, London, UK, Iliffe & Sons; pp. 253-254.
Escher, DJW, "Historical Aspects of Cardiac Pacing," Cardiac Pacing ($2^{nd}$ Ed.), Samet, P, et al., eds., New York, Grune & Stratton, 1979, pp. 631-643.
Etienne, Y, et al., "Evaluation of Left Ventricular Based Pacing in Patients With Congestive Heart Failure and Atrial Fibrillation," Am. J. Cardiol., vol. 83, 1999, pp. 1138-1140.
Fields, J. et al., "Surgical Experience With Temporary and Permanent A-V Sequential Demand Pacing," J. of Thoracic and Cardiovascular Surgery, vol. 66, No. 6, Dec. 1973, pp. 865-877.
Fletcher, FW, et al., "Effect of Pacemaker Location on Cardiac Function in Complete Heart Block," Am. J. Physiol., 1963; 205:1232-34.
Gabrielle, O.F., "Pacing via Coronary Sinus," N. Engl. J. Med., vol. 280, No. 4, 1969, p. 219.
Greenberg, et al., "Coronary Sinus Pacing: Clinical Follow-up," Circulation, vol. 57, No. 1, Jan. 1978, pp. 98-103.
Hayes, D. "Pacemakers" in Comprehensive Cardiovascular Medicine, EJ Topol, ed., Philadelphia, Lippincott-Raven Publishers, 1998, pp. 2099-2132.
Higgins SL, et al. "Cardiac Resynchronization Therapy for the Treatment of Heart Failure in Patients with Intraventricular Conduction Delay and Malignant Ventricular Tachyarrhythmias," J. Am. Coll. Cardiol., Vo. 42, No. 8, 2003, pp. 1454-1459.
Holmes, DR, et al., "Pacemaker Implantation Techniques," in Electrical Therapy for Cardiac Arrhythmias, Saksena, S, et al., eds., Philadelphia, WB Saunders Co., 1990, pp. 173-190.
Kass DA, et al., Improved Left Ventricular Mechanics from Acute VDD Pacing in Patients with Dilated Cardiomyopathy and Ventricular Conduction Delay, Circulation, vol. 99, No. 12, Mar. 1999, pp. 1567-1573.
Kastor, J. et al., "Variations in Discharge Rate of Demand Pacemakers Not due to Malfunction," Am. J. of Cardiology, vol. 25, No. 3, Mar. 1970, pp. 344-348.
Keller, J. Walter, "Atrial and Ventricular Synchrony: The Engineering-Physiology Interface," Annals of the New York Academy of Sciences, vol. 167, 1969, pp. 869-885.
Leclercq C, et al., "Acute Hemodynamic Effects of Biventricular DDD Pacing in Patients with End-Stage Heart Failure," J. Am. Coll. Cardiol., vol. 32, No. 7, Dec. 1998, pp. 1825-1831.
Lemberg, L. et al., "Demand and Bifocall Demand Pacing," Singapore Med. J., vol. 14, No. 3, Sep. 1973, pp. 222.
Lemberg, L. et al., "Pacemaking on Demand in AV Block," JAMA, vol. 191, No. 1, Jan. 1965, pp. 106-108.
Lemberg, L., et al., "Systolic and Diastolic Pacemaker Induced Repetitive Firing in the Human Heart: Analysis of 23 Cases," J. Electrocardiology, vol. 2, No. 4, Oct. 1969, pp. 353-362.
Lown, B. et al., "Comparison of Alternating Current with Direct Current Electroshock Across the Closed Chest," Am. J. of Cardiology, Aug. 1962, pp. 223-233.
Lurie KL, et al., "Development of Multifunctional Coronary Sinus Catheter," RBM (Revue Europeenne De Technologie Biomedicale) 1994, 16:159-61.
Mansourati J, et al., "Left Ventricular-Based Pacing in Patients With Chronic Heart Failure: Comparison of Acute Heodynamic Benefits According to Underlying Heart Disease," European Journal of Heart Failure, 2(2000):195-99.
Maytin, O., et al., "Diagramatic Representation of Pacemaker Arrhythmias," J. Electrocardiology, vol. 3, No. 3-4, 1970, pp. 251-257.
Medina-Ravell, V. et al., "Management of Tachyarrhythias with Dual-Cahmber Pacemakers," PACE, vol. 6, No. 2, Mar.-Apr. 1983, Part II, pp. 333-345.
Medina-Ravell, V. et al., "Use of Dual-Demand AV Sequential (DVI, MN) Pacemakers in the Management of Supraventricular Tachycardias," Pacemaker Therapy, L. Dreifus ed., 1983, pp. 227-238.
Medtronic Model 5330 A-V Sequential Demand Pulse Generator, Technical Manual, Jun. 1978.
Miyazawa, K. et al., "Effects of Varying Pacemaker Sites on Left Ventricular Performance," Tohoku J. exp. Med., 1976, 120. 301-08.
Miyazawa, K. et al., "Regional Contraction Patterns of the Left Ventricle During Ventricular Pacing," Tohoku J. exp. Med. 1977, 122; pp. 167-174.
Moss, AJ. et al., "Atrial Pacing from the Coronary Vein: Ten-Year Experience in 50 Patients with Implanted Pervenous Pacemakers," Circulation, vol. 57, No. 1, 1978, pp. 103-106.
Nelson, GS, et al., "Left Ventricular or Biventricular Pacing Improves Cardiac Function at Diminished Energy Cost in Patients with Dilated Cardiomyopathy and Left Bundle-Branch Block," Circulation, vol. 102, 2000, pp. 3053-3059.
Ogawa, S. et al., "Hemodynamic Consequences of Atrioventricular and Ventriculoatrial Pacing," PACE, vol. 1, No. 1, Jan.-Apr. 1978, pp. 8-15.
Popovic ZB, et al., "Noninvasive Assessment of Cardiac Resynchronization Therapy for Congestive Heart Failure Using Myocardial Strain and Left Ventricular Peak Power as Parmeters of Myocardial Synchrony and Function," J. Cardiovase Electrophy., vol. 13, No. 12, 2002, pp. 1203-1208.
Portillo, B, et al., "Treatment of Drug Resistant A-V Reciprocating Tachycardias With Multiprogrammable Dual Demand A-V Sequential (DVI, MN) Pacemakers," PACE, vol. 5, No. 6, 1982, pp. 814-825.
Prauer, H, et al., "Prolonged Electrostimulation of the Heart Through the Coronary Sinus; Report of Two Cases with Postion of the Electrode Confirmed by Autopsy," Thoraxchirugie Vaskulare Chirurgie, 1974, 22, p. 207.
Program of the VIIth World Symposium on Cardiac Pacing, Vienna, May 1-5, 1983. in Schrittmacher: German Journal of Cardiac Pacing, Apr. 1983, listing De Teresa et al., "An Even More Physiological Pacing Changing the Sequence of Ventricular Activation."
Rodriguez Bailon, I., et al., "Some Data for an Unanswered Question: Choosing the Ventricular Electrode Place," PACE, vol. 8, No. 3, Part II, May 1985, p. A-11.
Rogel, S., et al., "Atrioventricular Time Sequence and Myocardial Efficiency," Archives Internationales de Physiologie et de Biochimie, 1973, 81, 833-42.
Romero, L., et al., "Non-Invasive Evaluation of Ventricular Function and Volumes During Atrioventricular Sequential and Ventricular Pacing," PACE, vol. 7, No. 1, Jan. 1984, pp. 10-17.
Program of International Congress of Cardiology, Marrakesh, Morocco, Nov. 4, 1988, listing Silva et al, "Biventricular Stimulation: An Approach to Physiologic Cardiac Stimulation."
Silva et al., "Epicardial Biventricular Stimulation Mimicking Activation During Sinus Rhythm. Experimental Study" European Heart Journal, vol. 8, Supp. 2, Sep. 1987, p. 180.
Smyth, et al., "Permanent Pervenous Atrial AV Synchronous and AV Sequential Pacing," Cardiac Pacing, Thalen, H, ed., Van Gorcum: Assen, Netherlands, 1973, p. 145.

(56) References Cited

OTHER PUBLICATIONS

Stokes, K. et al. "The Electrode-Biointerface: Stimulation," Modern Cardiac Pacing, Barold, SS, ed., Futura Publishing, 1985, pp. 33-78.

Sutton, R, et al., "Appendix 1: The History of Cardiac Pacing," The Foundations of Cardiac pacing, Futura Publishing, Mt. Kisco, NY, 1991, pp. 319-324.

Young JB, et al., "Combined Cardiac Resynchronization and Implantable Cardioversion Defibrillation in Advanced Chronic Heart Failure: The MIRACLE ICD Trial," JAMA, vol. 238, No. 20, pp. 2685-2694.

Zaroff, L, et al., "An Implantable Demand Pacemaker," The Annals of Thoracic Surgery, vol. 4, No. 5, Nov. 1967, pp. 463-467.

Zoll, P, "Resuscitation of the Heart in Ventricular Standstill by External Electrical Stimulation," N. Engl. J. Med., vol. 247, No. 20, 1952, pp. 768-771.

Zuckerman, W. et al., "Clinical Applications of Demand Pacing," Annals of the New York Academy of Sciences, vol. 167, No. 2, Oct. 30, 1969, pp. 1055-1059.

Zuckerman, W, et al., "Clinical Experiences with a New Implantable Demand Pacemaker," Am. J. of Cardiology, vol. 20, Aug. 1967, pp. 232-238.

European Office Action issued Aug. 9, 2013, in European Patent Application No. 09 158 987.9.

* cited by examiner

METHODS, APPARATUS, AND SYSTEMS FOR MULTIPLE STIMULATION FROM A SINGLE STIMULATOR

CROSS-REFERENCE TO RELATED APPLICATIONS

This application is a continuation application of U.S. patent application Ser. No. 11/745,593, filed May 8, 2007, now U.S. Pat. No. 8,249,725, the entire content of which is incorporated herein by reference. U.S. patent application Ser. No. 11/745,593 is a divisional of U.S. patent application Ser. No. 10/625,526, filed Jul. 24, 2003, now U.S. Pat. No. 7,231,249.

DESCRIPTION OF THE INVENTION

1. Field of the Invention

The present invention relates to cardiac stimulators, and in particular, to methods, apparatus, and systems for pacing multiple sites in a heart.

2. Background

During a normal heartbeat, the heart contracts in a coordinated fashion to pump blood. In particular, the heart contracts based on rhythmic electrical impulses, which are spread over the heart using specialized fibers. These rhythmic electrical pulses are initiated by the heart's natural pacemaker called the sinoatrial node ("SA node"). The SA node initiates electrical impulses to cause the right and left atrium to contract. As the atria contract, the electrical impulses from the SA node propagate to the atrial-ventricular node ("AV node"). After an inherent delay in the AV node, the AV node then transmits the electrical impulses, which eventually causes contraction in the right and left ventricles. The inherent delay of the AV node is known as the A-V delay and allows the atria to fully contract and fill the ventricles with blood. Blood from the ventricles then flows out of the heart and to the rest of the body. Therefore, the heart relies upon a rhythmic cycle of electrical impulses to pump blood efficiently.

A heart may suffer from one or more cardiac defects that interfere with the rhythmic cycle or conduction of electrical impulses. For example, one known heart condition is an AV nodal block. An AV nodal block inhibits transfer of impulses from the SA node to the AV node, and thus, inhibits or prevents contraction of the right and left ventricles. Other conditions, such as myocardial scarring and bundle branch block, may slow conduction of impulses, and thus, cause the heart to beat in an uncoordinated fashion.

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In such cases, the right and left heart chambers do not contract in optimum synchrony with one another, and cardiac output suffers.

Typically, an artificial pacemaker is installed to treat these and other various cardiac deficiencies. For example, in the case of loss of A-V synchrony, a single chamber, demand pacemaker may sense impulses from the SA node and then supply stimulating electrical pulses to the ventricles to cause contraction in the right and left ventricles. In this manner, an artificial pacemaker may compensate for blocked or slowed conduction of electrical impulses from the atrium to the ventricles in the heart.

Dual chamber, demand pacemakers typically supply pacing pulses when required to one upper heart chamber and to one lower heart chamber, usually the right atrium and the right ventricle. In a dual chamber, demand pacemaker operating in DDD pacing mode, an atrial pacing pulse is delivered to the atrium if an atrial contraction is not sensed within an atrial escape interval (A-A interval) and a ventricular pacing pulse is delivered to the ventricle if a ventricular contraction is not sensed within a ventricular escape interval (V-V interval).

Patients suffering from congestive heart failure and other conduction defects may require bi-ventricular and/or bi-atrial pacing. For example, in a dual chamber bi-atrial pacemaker, the right atrium may be paced at the expiration of an A-A escape interval, and the left atrium is synchronously paced or paced after a short delay. In a dual chamber bi-ventricular pacemaker, the right ventricle may be paced at the expiration of a V-V escape interval, and the left ventricle is synchronously paced or paced after a short delay time. In a single chamber pacemaker with bi-chamber pacing, a pacing pulse delivered at the end of an AV delay may trigger the simultaneous or slightly delayed delivery of the pacing pulse to the other heart chamber.

In order to provide stimulating electrical pulses, known artificial pacemakers may include multiple stimulators. Furthermore, an artificial pacemaker may include multiple stimulators that are triggered at different times to provide dual chamber and/or bi-chamber pacing. Unfortunately, providing and controlling multiple stimulators increases the number of components that may fail within an artificial pacemaker.

Accordingly, it would be desirable to provide methods, apparatus, and systems, which can avoid using multiple stimulators and overcome other deficiencies in the prior art.

SUMMARY OF THE INVENTION

In accordance with an aspect of the present invention, a dual chamber cardiac pacemaker comprises a first electrode, a second electrode, a signal generator, a first lead, a second lead, and a distributor circuit. The first electrode electrically is coupled to an atrial chamber. The second electrode is electrically coupled to a ventricular chamber. The signal generator generates a sequential pair of electrical pacing pulses. The first lead is coupled to the signal generator and to the first electrode and the second lead is coupled to the signal generator and to the second electrode. The distributor circuit is connected between the first lead and the signal generator and between the second lead and the signal generator. The distributor circuit receives the pair of electrical pacing pulses, distributes a first pacing pulse from the pair at a first amplitude to the first lead and distributes a second pacing pulse from the pair at a second amplitude to the second lead after a delay period.

In accordance with another aspect of the present invention, a bi-chamber cardiac pacemaker comprises a first electrode, a second electrode, and a lead. The first electrode is electrically coupled to a left chamber and the second electrode is electrically coupled to a right chamber. The signal generator generates pacing pulses. The lead couples the signal generator to the first electrode and includes a distal end to be coupled to the second electrode. The lead further includes a delay element between the first electrode and the second electrode. The delay element prevents the second electrode from receiving a pacing pulse until after a predetermined delay period.

In accordance with another aspect of the present invention, a bi-chamber cardiac pacemaker comprises a first electrode, a second electrode, a signal generator, a first lead, a second lead, and a distributor circuit. The first electrode is electrically coupled to a left chamber. The second electrode is electrically coupled to a right chamber. The signal generator generates a sequential pair of electrical pacing pulses. The first lead couples the signal generator and the first electrode. The second lead couples the signal generator and the second electrode. The distributor circuit is connected between the first lead and the signal generator and between the second lead and the signal generator. The distributor circuit receives the pair of electrical pacing pulses, distributes a first pacing pulse of the pair at a first amplitude to the first lead, and distributes a second pacing pulse of the pair at a second amplitude to the second lead after a delay period.

In accordance with yet another aspect of the present invention, a bi-chamber cardiac pacemaker comprises a first electrode, a second electrode, a signal generator, a first lead, a second lead, and a distributor circuit. The first electrode electrically is coupled to a left chamber and the second electrode is electrically coupled to a right chamber. The signal generator generates an electrical pulse. The first lead couples the signal generator and the first electrode. The second lead couples the signal generator and the second electrode. The distributor circuit is connected between the first lead and the signal generator and between the second lead and the signal generator. The distributor circuit distributes pacing pulses to the first lead at a first amplitude and to the second lead at a second amplitude in response to the electrical pulse generated by the signal generator.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention. In the figures.

DESCRIPTION OF THE EMBODIMENTS

Methods, apparatus, and systems are provided to control contraction of the heart. In particular, a controller is provided with a distributor that is configured to distribute stimulating signals to multiple sites in a heart via one or more leads. In addition, the controller may vary the timing of the stimulating signals such that stimulation of the multiple sites in the heart occurs with a delay. Methods, apparatus, and systems consistent with the present invention may provide dual chamber pacing (for example, DDD or DDI), bi-chamber pacing (i.e., bi-ventricular or bi-atrial), multiple stimulation to a single chamber, or any desired combination of these pacing modalities.

Reference will now be made in detail to exemplary embodiments of the invention, examples of which are illustrated in the accompanying drawings. Wherever possible, the same reference numbers will be used throughout the drawings to refer to the same or like parts.

Figure 1:
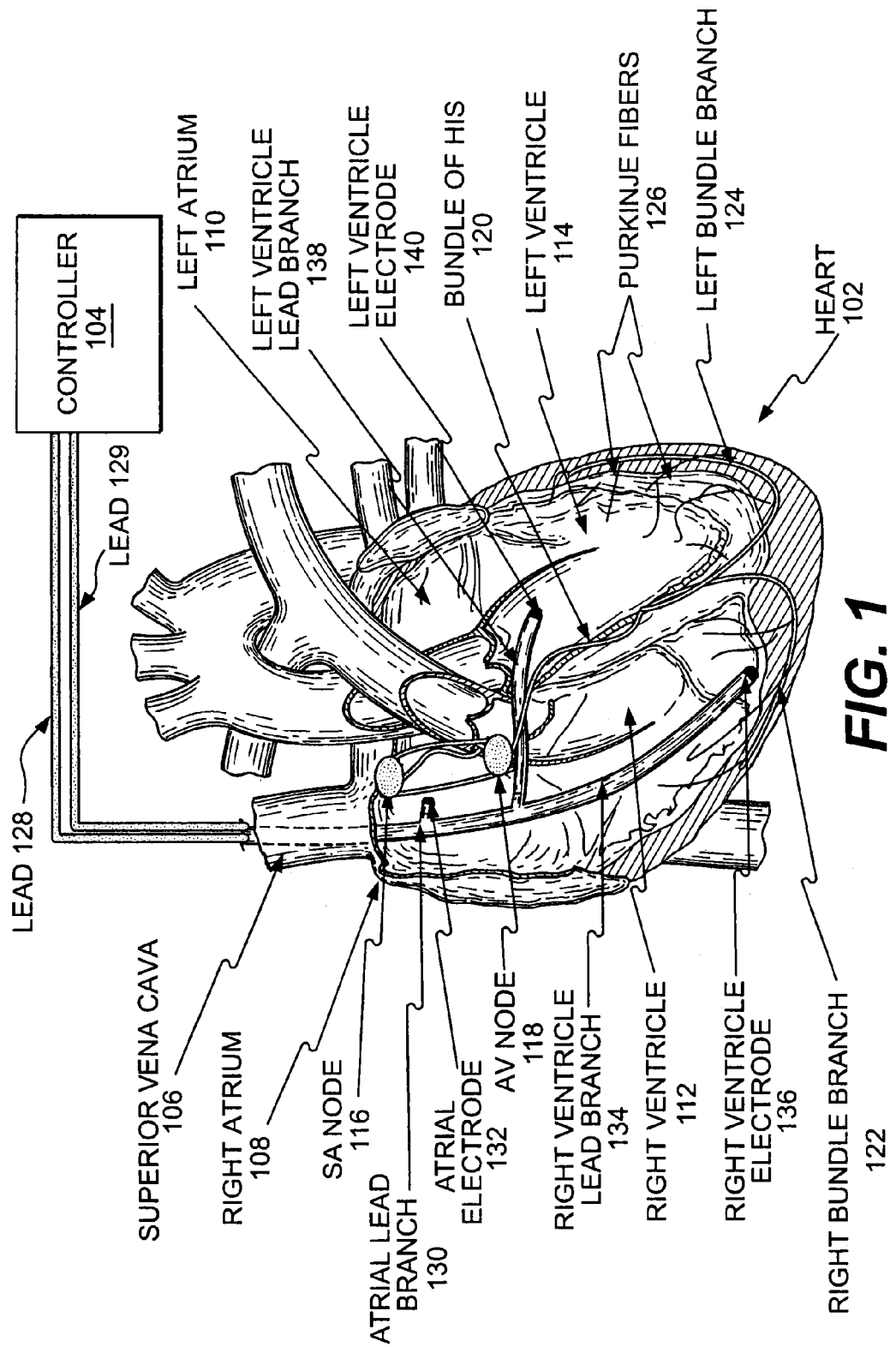
FIG. 1 illustrates an environment in which methods, apparatus, and systems may be applied consistent with the principles of the present invention.

FIG. 1 illustrates an environment in which methods, apparatus, and systems may be applied consistent with the principles of the present invention. As shown, a controller 104 may accompany a heart 102. In addition, heart 102 is shown with a superior vena cava 106, a right atrium 108, a left atrium 110, a right ventricle 112, a left ventricle 114, a sinoatrial node ("SA node") 116, an atrial-ventricular node ("AV node") 118, a Bundle of His 120, a right bundle branch 122, a left bundle branch 124, and Purkinje fibers 126.

Heart 102 normally contracts in two stages based on sinus rhythm. Sinus rhythm is where heart 102 contracts in response to electrical impulses generated from SA node 116. In order to cause contraction in the cardiac muscle of heart 102, the electrical impulses from SA node 116 must depolarize the muscle fibers above a threshold voltage of approximately −80 mV.

In particular, as electrical impulses propagate from SA node 116 to AV node 118, right atrium 108 and left atrium 110 contract. AV node 118 may then provide an AV delay of approximately 120 to 200 milliseconds that allows right ventricle 112 and left ventricle 114 to fill with blood.

After the AV delay, AV node 118 then emits another electrical impulse. This electrical impulse propagates relatively quickly over heart 102 down Bundle of His 120, and over right bundle branch 122, left bundle branch 124, and Purkinje fibers 126. In response, cardiac muscles in right ventricle 112 and left ventricle 114 depolarize and contract to pump blood to the rest of the body (not shown).

Controller 104 assists heart 102 to contract in a coordinated fashion based, for example, on sinus rhythm. Controller 104 may assist heart 102 by applying one or more electrical pulses to one or more sites in heart 102 and cause contraction in the chambers of heart 102, such as right ventricle 112 and left ventricle 114. Controller 104 may vary the timing that the stimulating electrical pulses are applied to heart 102. In addition, controller 104 may be configured to selectively apply the stimulating electrical pulses to one or more of the sites in heart 102.

As shown in FIG. 1, controller 104 may be coupled to heart 102 using leads 128 and 129. Leads 128 and 129 may be installed endocardially into heart 102 via superior vena cava 106 using known surgical procedures. Leads 128 and 129 may be implemented as a hollow catheter made of an insulating material, such as silicone rubber, and include one or more connection paths made of a conductive material, such as a wire made of stainless steel or other metal. The one or more connection paths of leads 128 and 129 may carry signals back and forth between heart 102 and controller 104. For example, the one or more connection paths of leads 128 and 129 may carry signals that represent the electrical activity of heart 102 from heart 102 to controller 104. In addition, the one or more connection paths of leads 128 and 129 may carry electrical signals, such as stimulating electrical pulses, from controller 104 to heart 102.

For example, in one embodiment, lead 128 may be structured to include an atrial lead branch 130, an atrial electrode 132, a right ventricle lead branch 134, and a right ventricle electrode 136. Lead 129 may be structured to include a left ventricle lead branch 138 and a left ventricle electrode 140. Although FIG. 1 illustrates two leads (i.e., leads 128 and 129), any number of leads may be used to couple controller 104 to heart 102. In addition, each lead may include any number of connection paths, e.g., wires.

Atrial lead branch 130 of lead 128 provides a connection path between controller 104 and right atrium 108 for carrying signals associated with right atrium 108 and SA node 116 from heart 102 to controller 104 and for carrying stimulating electrical signals from controller 104 to heart 102. Although atrial lead branch 130 is shown as a branch of lead 128, atrial lead branch 130 may be implemented using a separate lead from controller 104.

Atrial electrode 132 is provided at the tip of atrial lead branch 130 and physically contacts one or more sites in right atrium 108. Atrial electrode 132 senses the electrical activity in heart 102 associated with right atrium 108 and SA node 116. In addition, atrial electrode 132 delivers the stimulating electrical signals from controller 104 to right atrium 108. Atrial electrode 132 may be implemented, for example, as a helical coil of wire made of a metal, such as stainless steel. Atrial electrode 132 may be implemented using other known structures and may also comprise a plurality of electrodes.

Right ventricle lead branch 134 of lead 128 provides a connection path for carrying signals associated with right ventricle 112 from heart 102 to controller 104 and for carrying stimulating electrical signals from controller 104 to right ventricle 112. Although right ventricle lead branch 134 is shown as a branch of lead 128, right ventricle lead branch 134 may be implemented using a separate lead from controller 104.

Right ventricle electrode 136 is provided at the tip of right ventricle lead branch 132 and physically contacts one or more sites in right ventricle 112. Right ventricle electrode 136 senses the electrical activity in heart 102 associated with right ventricle 112, such as electrical impulses from AV node 118 that are propagating over right bundle branch 122. In addition, right ventricle electrode 136 delivers the stimulating electrical signals from controller 104 to right ventricle 112. Right ventricle electrode 136 may be implemented, for example, as a helical coil of wire made of a metal, such as stainless steel. Right ventricle electrode 136 may be implemented using other known structures and may also comprise a plurality of electrodes.

Left ventricle lead branch 138 of lead 129 provides a connection path for carrying signals associated with left ventricle 114 from heart 102 to controller 104 and for carrying electrical signals from controller 104 to left ventricle 114. Although left ventricle lead branch 138 is shown as a branch of lead 129, left ventricle lead branch 138 may also be implemented using a separate lead from controller 104.

Left ventricle electrode 140 is provided at the tip of left ventricle lead branch 138 and physically contacts one or more sites in left ventricle 114. Left ventricle electrode 140 senses electrical activity in heart 102 associated with left ventricle 114, such as electrical impulses from AV node 118 that are propagating over left bundle branch 124. Left ventricle electrode 140 may be implemented, for example, as a helical coil of wire made of a metal, such as stainless steel. Left ventricle electrode 140 may be implemented using other known structures and may also comprise a plurality of electrodes.

The lead configuration illustrated in FIG. 1 is but one example for providing bi-chamber stimulation. One of ordinary skill will appreciate that methods, systems, and apparatus consistent with the present invention may use any lead configuration that allows for stimulation of any combination of chambers or sites in heart 102. By way of example only, the leads of controller 104 could provide for sensing and/or pacing in (1) right ventricle 112 and right atrium 108, (2) left ventricle 114 and left atrium 110, (3) right ventricle 112 and left ventricle 114, (4) the right and left atria 108 and 110, respectively, (5) two sites in a single chamber, such as left ventricle 114, or any combination of the above.

Figure 2:
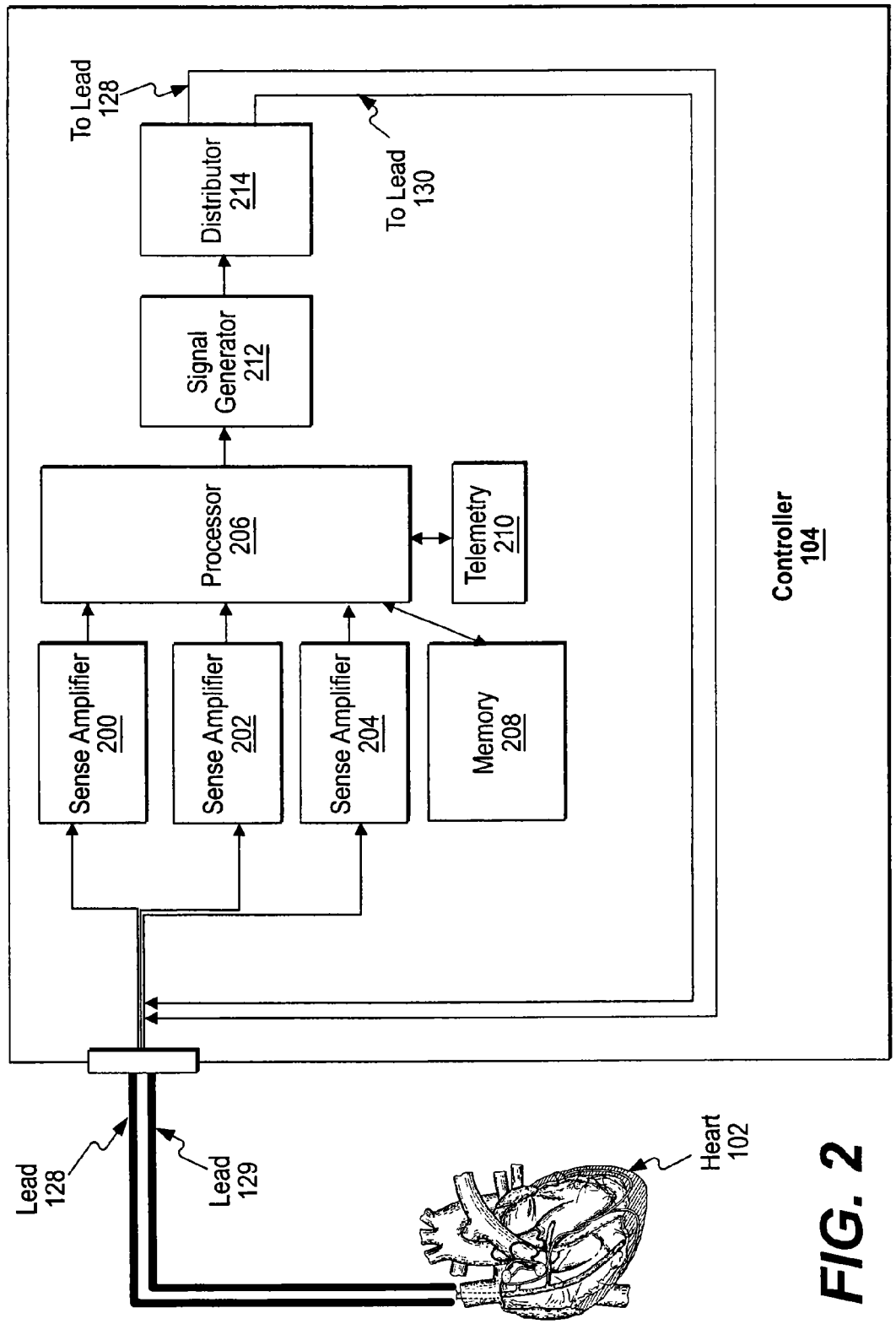
FIG. 2 illustrates a functional block diagram of a controller with multiple leads for controlling contraction of a heart consistent with the principles of the present invention.

FIG. 2 illustrates a functional block diagram of controller 104 with multiple leads for controlling contraction of heart 102 consistent with the principles of the present invention. As shown, controller 104 includes sense amplifiers 200, 202, and 204, a processor 206, a memory 208, a telemetry module 210, a signal generator 212, and a distributor 214.

Sense amplifiers 200, 202, and 204 are coupled via lead 128 to atrial electrode 132, right ventricle electrode 136, and left ventricle electrode 140, respectively. Sense amplifiers 200, 202, and 204 receive signals indicating electrical activity of heart 102 from their respective electrodes, amplify these signals, and provide them to processor 206. Sense amplifiers 200, 202, and 204 may be implemented using, for example, well known circuitry.

Processor 206 receives and monitors signals from sense amplifiers 200, 202, and 204 and generates one or more control signals. For example, processor 206 may detect the sinus rhythm of heart 102 based on signals received from atrial electrode 132. Processor 308 may then monitor the electrical activity of right ventricle 112 and left ventricle 114 based on signals received from right ventricle electrode 136 and left ventricle electrode 140. If the electrical activity in right ventricle 112 fails to reach a threshold level within a period of time corresponding, for example, to a desired A-V delay period, then processor 206 may be configured to provide one or more control signals to signal generator 212. The one or more control signals then command signal generator 212 to deliver one or more stimulating electrical pacing pulses to chambers of heart 102, such as right ventricle 112 and/or left ventricle 114.

Alternatively, processor 206 may be configured to provide the one or more control signals to signal generator 212 automatically. For example, upon detecting the sinus rhythm of heart 102 based on signals received from atrial electrode 132, processor 206 may be configured to automatically provide the one or more control signals that commands signal generator 212 to stimulate one or more chambers of heart 102, such as right ventricle 112 and left ventricle 114, automatically.

Processor 206 may be implemented using known devices. For example, processor 206 may be implemented using a series of digital circuits or logic gates. Alternatively, processor 206 may be implemented using a microprocessor, such as those manufactured by the Intel Corporation.

Memory 208 provides storage for information used by processor 206. For example, memory 208 may include instructions for configuring processor 206 and instructions for monitoring the electrical activity of heart 102. Memory 208 may be implemented using known types of memory, such as a random access memory and read-only memory.

Telemetry module 210 provides diagnostic information indicating the performance of controller 104. For example, telemetry module 210 may transmit the signals received from sense amplifiers 200, 202, and 204, and signals generated by signal generator 212 via a radio link to another device, such as an external programmer (not shown). Telemetry module 210 may also collect and transmit other types of information. Telemetry module 210 may be implemented as a radio receiver/transmitter using a known radio frequency, such as 100 kHz.

Signal generator 212 generates electrical pulses for treating heart 102, for example, via lead 128. The electrical pulses from signal generator 212 may be delivered to, for example, right ventricle 112 and left ventricle 114 respectively via right ventricle lead branch 134 and left ventricle lead branch 138 of lead 128. In particular, signal generator 212 may provide, for example, a cathodal pulse of 5 V for a duration of approximately 2 milliseconds to stimulate contraction in heart 102.

When treating heart 102, signal generator 212 may vary the electrical pacing pulses delivered to heart 102. Signal generator 212 may vary the number of pulses, the pulse amplitude, and pulse width. For example, signal generator 212 may generate electrical pacing pulses in sequential pairs to stimulate contraction in one or more chambers of heart 102, such as right atrium 108 and right ventricle 112. Alternatively, signal generator 212 may manipulate the pulse amplitude and duration of its pulses in response to conditions measured from heart 102. Signal generator 212 may also use other types of pulses, such as biphasic pulses or anodal pulses, to stimulate contraction in heart 102.

In one embodiment, signal generator 212 is implemented using known circuitry, such as "one-shot" circuitry, that is triggered by processor 206. Alternatively, signal generator 212 may be implemented using other known components, such as a capacitor coupled to a continuous charger.

Distributor 214 receives the electrical pacing pulses from signal generator 212 and, in response, distributes the one or more electrical pacing pulses to one or more chambers of heart 102, such as right ventricle 112, left ventricle 114, etc., based on one or more control signals from processor 206. When distributing pulses, distributor 214 may vary the delay time between pulses, or inhibit one or more of the pulses based on the control signals from processor 206. One skilled in the art would also recognize that distributor 214 may vary other characteristics of the pulses, such as the amplitude, based on the control signals from processor 206.

Distributor 214 may be configured in various ways to manipulate the distribution of the electrical pulses to heart 102. For example, distributor 214 may be implemented using a variety of circuits and digital logic, such as flip-flops, multiplexers, Schmidt triggers, etc. Various examples of distributor 214 are described in more detail with reference to FIGS. 6-8.

Figure 3:
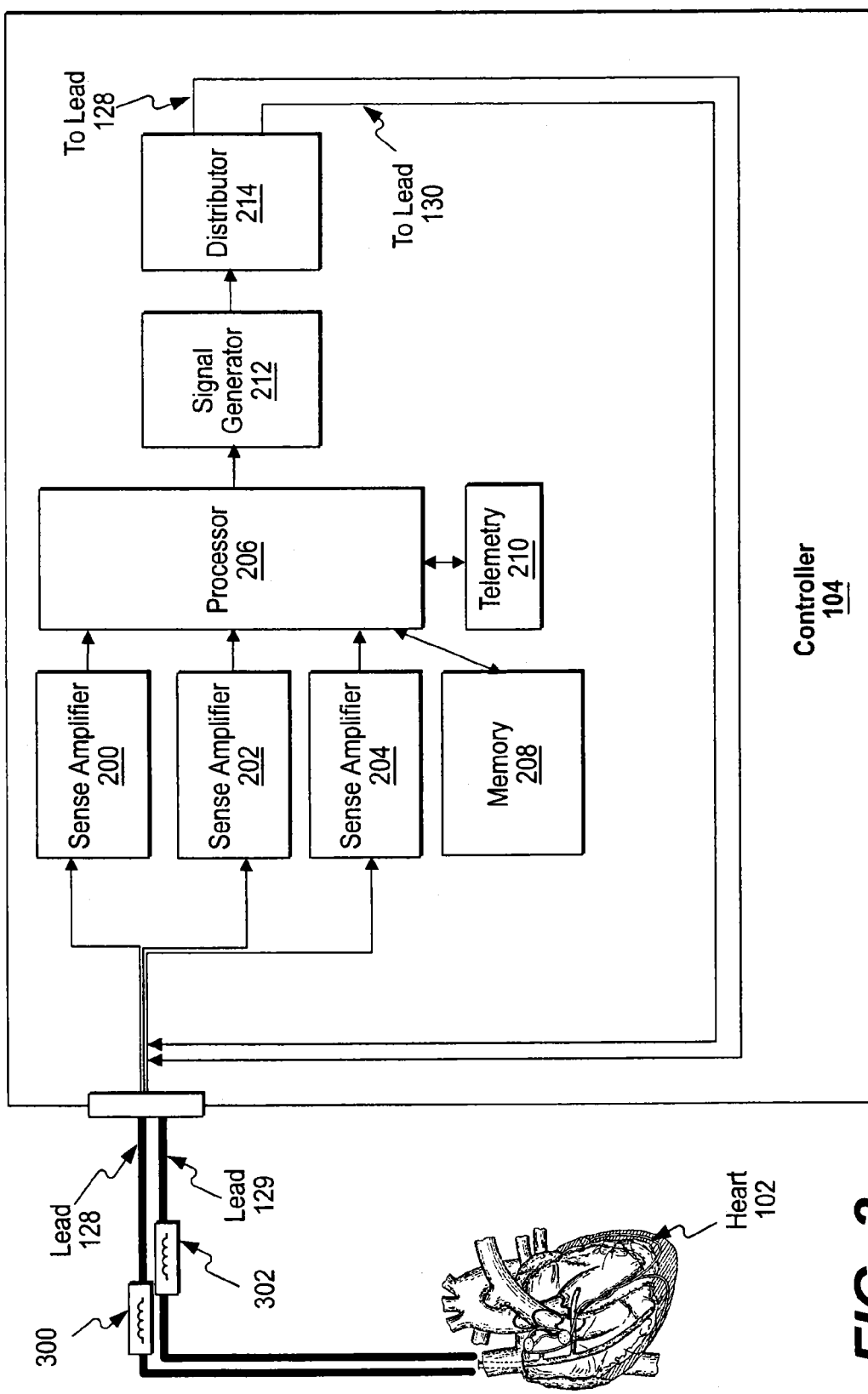
FIG. 3 illustrates an example of a controller with multiple leads having internal delay elements consistent with the principles of the present invention.

FIG. 3 illustrates a block diagram of one embodiment of controller 104 having multiple leads that include internal delay elements consistent with the principles of the present invention. In particular, delay elements 300 and 302 are shown within leads 128 and 129 respectively. Upon receiving electrical pacing pulses, delay elements 300 and 302 may delay the delivery of these pulses between right ventricle 112 and left ventricle 114, or between right atrium 108 and right ventricle 112, etc. In one embodiment, delay elements 300 and 302 are implemented as inductive elements to delay the delivery of pulses. One skilled in the art would also recognize that other types of components may be used within delay 300 and 302 to delay the delivery of pulses.

Figure 4:
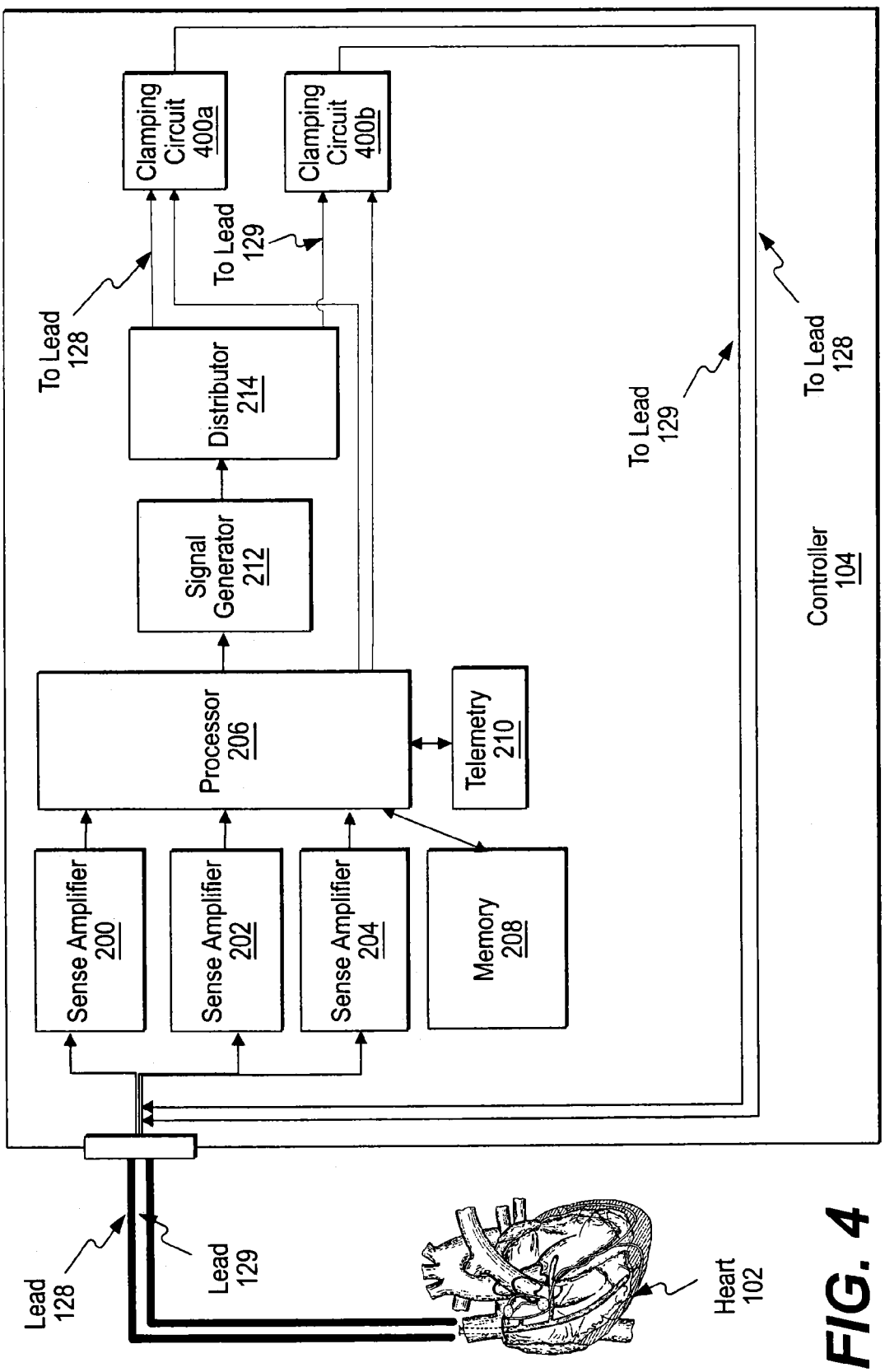
FIG. 4 illustrates a block diagram of an embodiment of a controller that includes multiple leads with respective clamping circuits consistent with the principles of the present invention.

FIG. 4 illustrates a block diagram of an embodiment of controller 104 that includes multiple leads with respective clamping circuits consistent with the principles of the present invention. As shown, controller 104 may include clamping circuits 400a and 400b at the output of distributor 214. Clamping circuits 400a-b allow controller 104 to selectively suppress or clamp the one or more electrical pacing pulses as they are output from distributor 214 and thereby vary the amplitude of a pulse or altogether inhibit application of a pulse. Use of clamping circuits 400a-b may be useful when, for example, controller 104 has detected spontaneous depolarization in a chamber of heart 102.

In particular, controller 104 may suppress or clamp the electrical pacing pulses when processor 206 detects spontaneous depolarization in heart 102 and determines that heart 102 does not require assistance based on signals received from electrodes 132, 136, and 140. The signals from electrodes 132, 136, and 140 may also indicate that the electrical impulses of sinus rhythm in heart 102 are propagating normally. Accordingly, processor 206 may send one or more control signals to clamping circuits 400a and/or 400b. In response, camping circuits 400a-b may then alter or suppress electrical pacing pulses output from distributor 214. Although clamping circuits 400a-b are shown connected at the output of distributor 214, clamping circuits 400a-b may be installed anywhere in controller 104, such as between signal generator 212 and distributor 214. Clamping circuits 400a-b are also described in more detail with reference to FIG. 9

Figure 5:
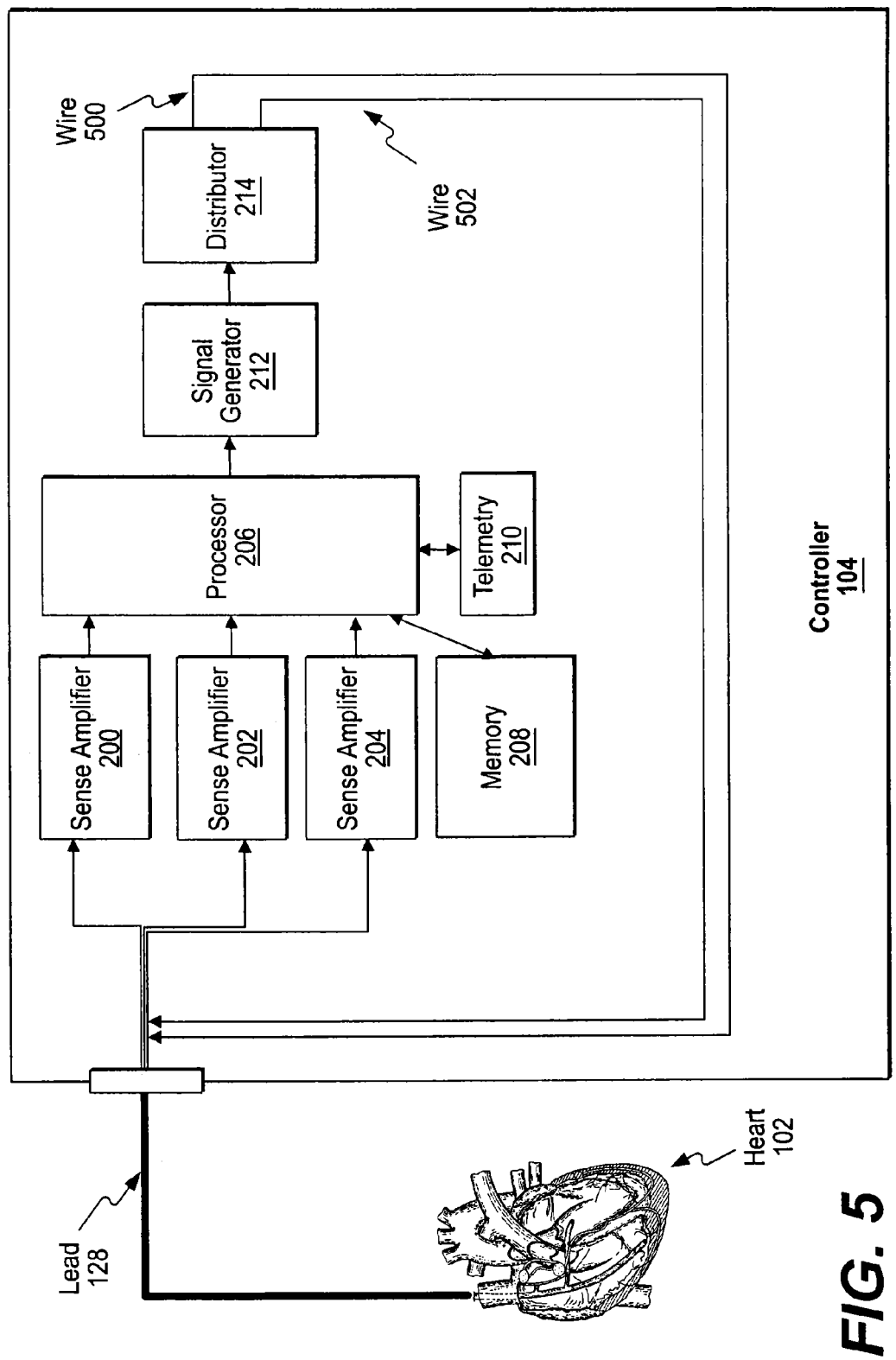
FIG. 5 illustrates a functional block diagram of a controller having a single lead with multiple wires consistent with the principles of the present invention.

FIG. 5 shows a block diagram of one embodiment of controller 104 having a single lead with multiple wires consistent with the principles of the present invention. In particular, controller 104 is coupled to heart 102 via a single lead, i.e., lead 128 instead of multiple leads as shown in FIGS. 1-4. In this embodiment, lead 128 further includes multiple wires, such as wires 500 and 502. Wires 500 and 502 provide respective connection paths to sites within heart 102, such as sites within right atrium 108, right ventricle 112 and/or left ventricle 114. Although FIG. 5 illustrates two wires within lead 128, i.e., wires 500 and 502, lead 128 may include any number of wires. Wires 500 and 502 may be constructed from known conductive materials, such as stainless steel, copper, or other metal. One skilled in the art would also recognize when controller 104 should be implemented with one lead having multiple wires or with multiple leads.

Figure 6:
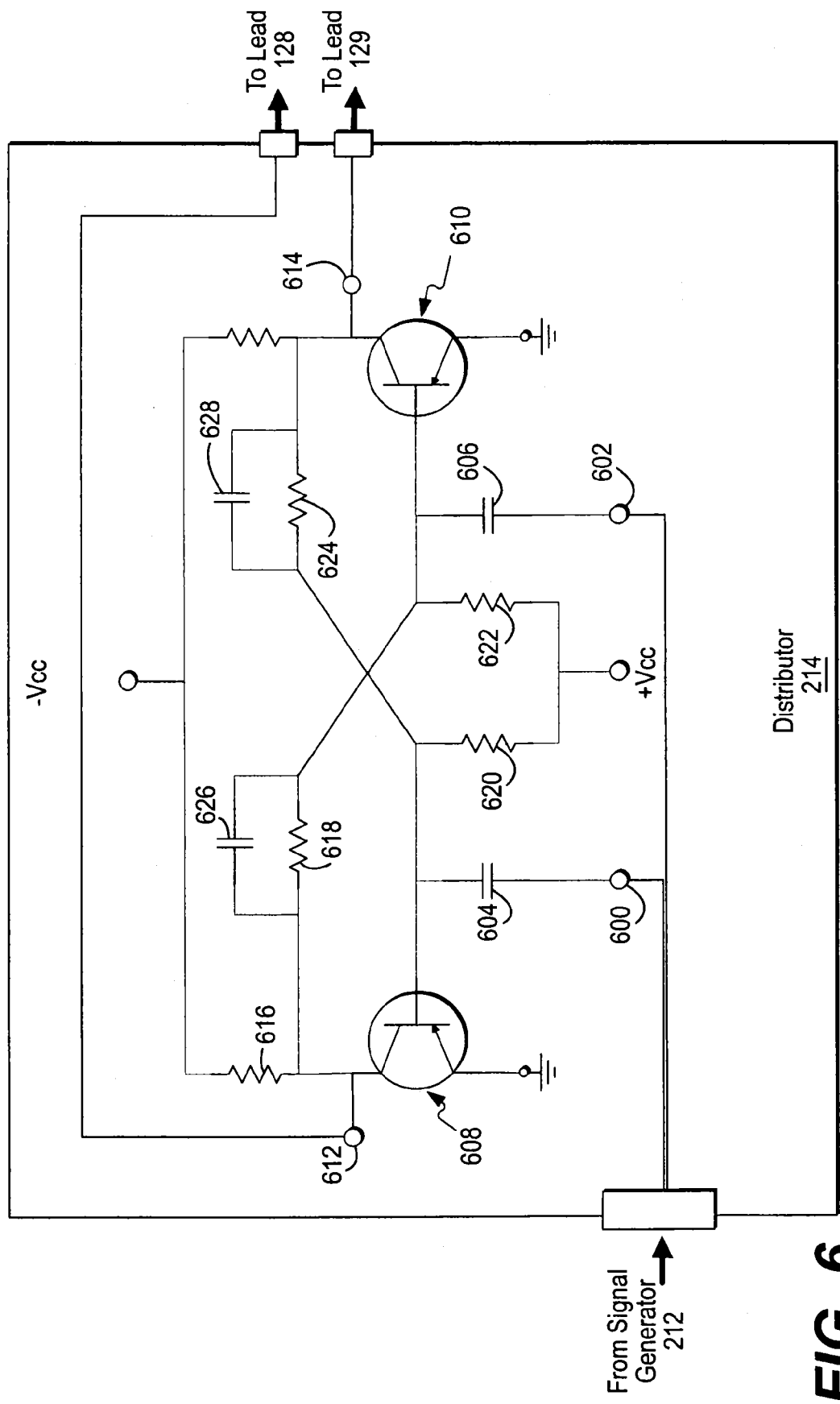
FIG. 6 illustrates an example of a distributor consistent with the principles of the present invention.

FIG. 6 illustrates an example of distributor 214 consistent with the principles of the present invention. As shown in FIG. 6, distributor 214 may be implemented as a bistable flip-flop that is triggered by one or more signals from signal generator 212. In particular, one or more signals from signal generator 212 are received at inputs 600 and 602. Capacitors 604 and 606 are coupled to inputs 600 and 602 respectively and charge and discharge in response to the one or more signals. The charge/discharge of capacitors 604 and 606 cause transistors 608 and 610 to turn on and then off. The cycling of transistors 608 and 610 subsequently generate electrical pacing pulses at outputs 612 and 614. Outputs 612 and 614 are then coupled to lead 128 and/or lead 129 to provide the electrical pacing pulses to one or more chambers of heart 102. Alternatively, when controller 104 is implemented with a single lead as shown in FIG. 5, outputs 612 and 614 may be coupled to wires 500 and 502 to provide the electrical pacing pulses to heart 102.

The characteristics of the electrical pacing pulses, such as their amplitude and pulse width, are determined based on the values of resistors 616, 618, 620, 622, and 624 and capacitors 626 and 628. The values of these components may be predetermined. Alternatively, distributor 214 may manipulate or set one or more of these values in response to control signals from processor 206. Resistors 616, 618, 620, 622, and 624 and capacitors 626 and 628 are implemented using known components. Moreover, distributor 214 may manipulate the above components to control the delay between pulses.

Figure 7:
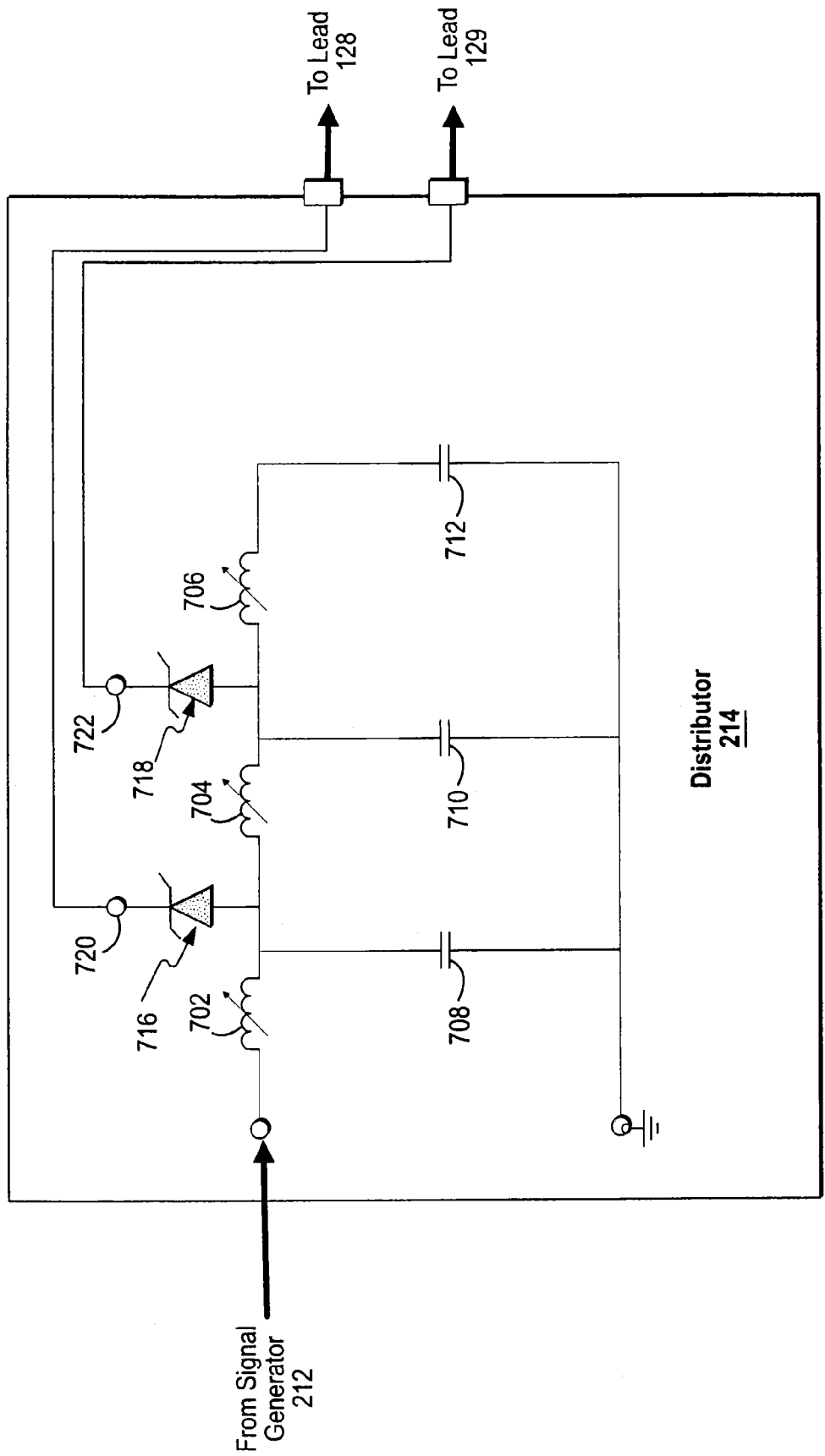
FIG. 7 illustrates another example of a distributor consistent with the principles of the present invention.

FIG. 7 illustrates another example of distributor 214 consistent with the principles of the present invention. As shown, distributor 214 may be implemented as an array of "LC" circuits comprising inductors 702, 704, and 706, and capacitors 708, 710, and 712. In particular, the signal from signal generator 212 may be used energize the LC circuits of distributor 214. In one embodiment, inductors 702, 704, and 706 may be set to a particular inductive value for a desired delay between electrical pacing pulses based on a control signal from processor 206. Processor 206 may determine the values for inductors 702, 704, and 706 based on information received via telemetry module 210.

In order to trigger application of the electrical pacing pulses, distributor 214 may include diodes 716 and 718, which are biased based on the voltage output of the LC circuits. For example, in one embodiment, diodes 716 and 718 may be implemented as Zener diodes that discharge when the respective LC circuits for diodes 716 and 718 reach a threshold voltage. Alternatively, diodes 716 and 718 may provide electrical pacing pulses based on a local electrical state of electrodes, such as electrodes 132, 136, and 140, within heart 102. In particular, diodes 716 and 718 may be implemented as silicon controlled rectifiers, which are gated based on control signals from processor 206. Processor 206 may generate the control signals in response to signals received from sense amplifiers 200, 202, and 204, which are coupled to electrodes 132, 136, and 140 respectively.

Upon reaching the threshold voltage, diodes 716 and 718 then discharge electrical pacing pulses to outputs 720 and 722. Outputs 720 and 722 are then coupled to lead 128 and/or lead 129 to provide the one or more electrical pacing pulses to one or more chambers of heart 102. Alternatively, when controller 104 is implemented with a single lead as shown in FIG. 5, outputs 720 and 722 may be coupled to wires 500 and 502 to provide the electrical pacing pulses to heart 102. One skilled in the art would also recognize that distributor 214 may vary the amplitude of the electrical pulses using, for example, known circuitry (not shown) or provide the electrical pulses at a single amplitude, for example, by implementing diodes 716 and 718 as Zener diodes.

Figure 8:
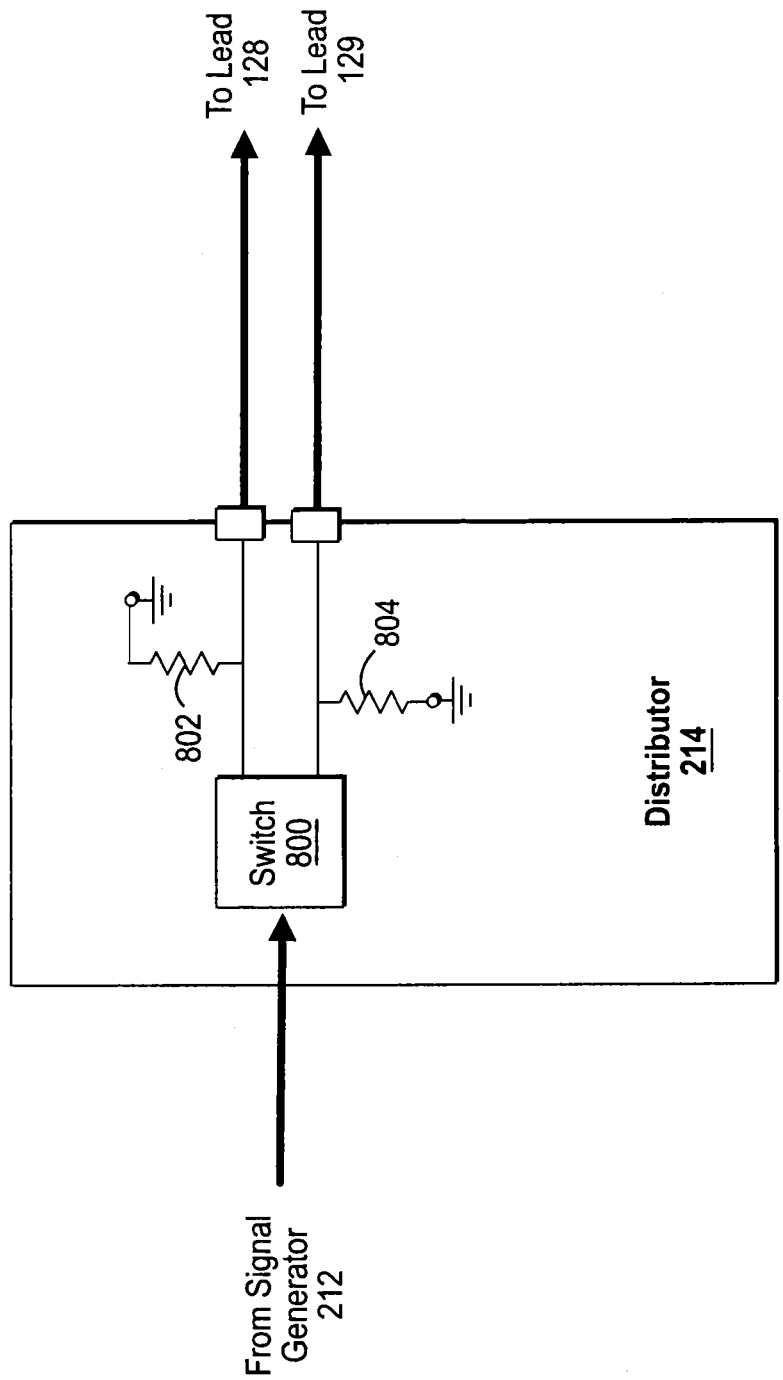
FIG. 8 illustrates another example of a distributor consistent with the principles of the present invention.

FIG. 8 illustrates another exemplary distributor 214 consistent with the principles of the present invention. As shown, distributor 214 may include a switching element 800 that routes the one or more electrical pulses from signal generator 212 to leads 128 and 129. In addition, distributor 214 may also include shunt resistors 802 and 804 to set the amplitude of pulses delivered to leads 128 and 129 respectively. The value of resistors 802 and 804 may, for example, be set in response to control signals from processor 206. Resistors 802 and 804 may be implemented using known components.

Switching element 800 may be implemented using known components, such as transistors or thyristors. Alternatively, switching element 800 may include a unistable electronic switch, which is followed by a bistable flip-flop to distribute electrical pacing pulses to leads 128 and 129. When controller 104 is implemented with a single lead as shown in FIG. 5, one skilled in the art would also recognize that the output of switch 800 may be coupled to wires 500 and 502 to provide electrical pacing pulses to heart 102.

Switching element 800 may distribute electrical pacing pulses based on a delay, for example, in response to control signals from processor 206. The delay may be a predetermined amount or specified by the one or more control signals from processor 206. In this embodiment, distributor 214 may also include other circuitry, such as a one-shot circuit (not shown) and threshold comparators, for example, to vary the delay between the pulses delivered to the right ventricle electrode 136 and left ventricle electrode 140.

Figure 9:
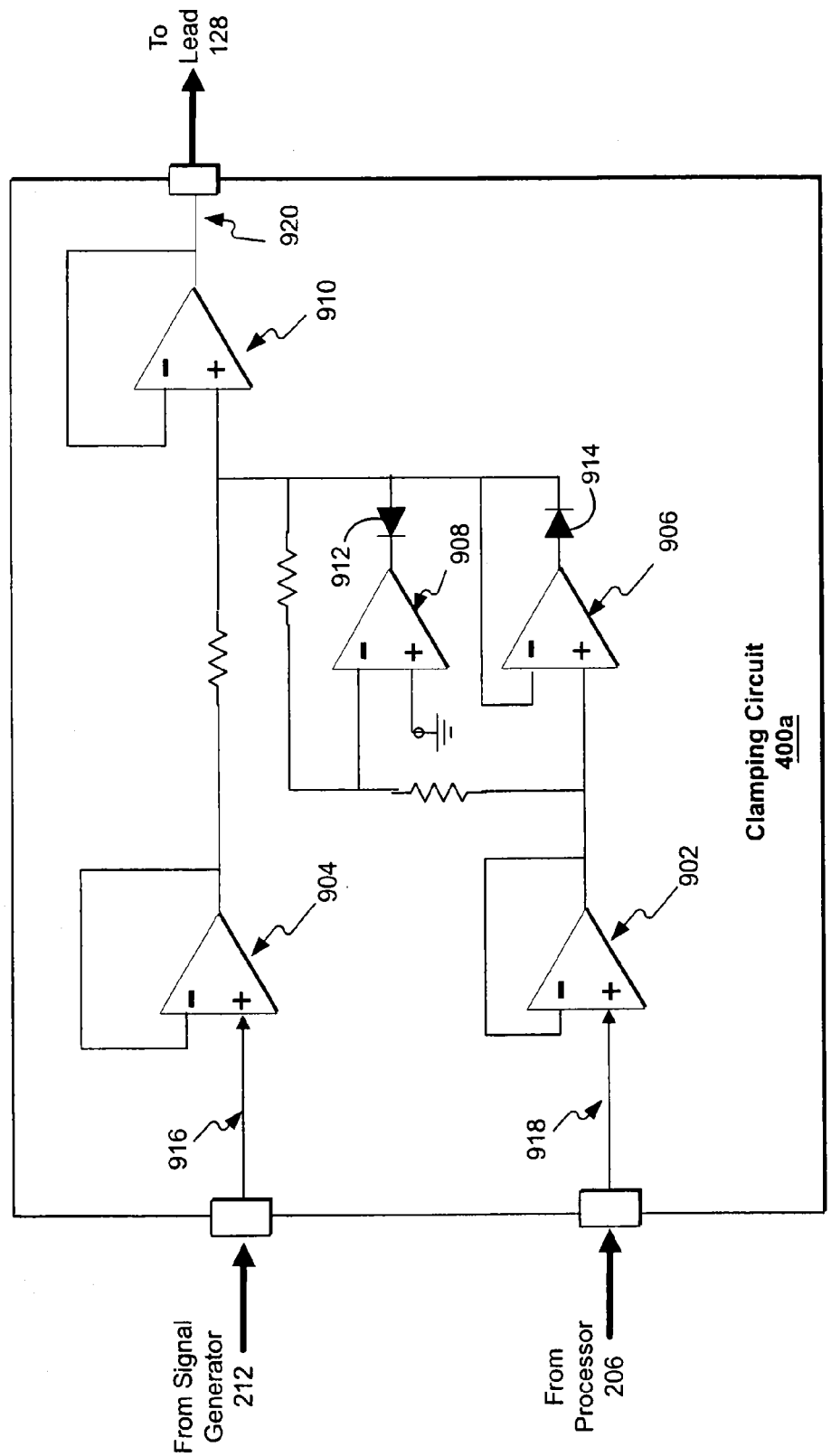
FIG. 9 illustrates a block diagram of a signal generator that includes a clamping circuit consistent with the principles of the present invention.

FIG. 9 illustrates an example of clamping circuits 400a-b consistent with the principles of the present invention. As described below, clamping circuit 400a (or 400b) clamps or suppresses a signal, such as the output of distributor 214, in response to a control signal (i.e., a clamping signal) from processor 206. As shown, in one embodiment, clamping circuit 400a may include components, such as operational amplifiers 902, 904, 906, 908, and 910, and diodes 912 and 914.

Clamping circuit 400a receives an input signal 916 from distributor 214 and a clamping signal 918 from processor 206. Input signal 916 is fed to operational amplifier 904, which is configured as a unity-gain buffer. The output of operational amplifier 904 is then fed to an input of operational amplifier 910 and the outputs of operational amplifiers 906 and 908 via diodes 914 and 912 respectively. The output of operational amplifier 904 is also fed back to inputs of operational amplifiers 906 and 908.

Clamping signal 918 is fed to operational amplifier 902, which is also configured as a unity-gain buffer. The output of operation amplifier 902 is then provided to inputs of operational amplifiers 906 and 908. Operational amplifiers 906 and 908 operate in conjunction with diodes 914 and 912 to clamp or suppress input signal 916 based on the relative values for input signal 916 and clamping signal 918.

For example, when input signal 916 is less than clamping signal 918, operational amplifiers 906 and 908 and diodes 914 and 912 are biased such that pacing signal 920 will be substantially the same value as input signal 916. Clamping circuit 900 then outputs pacing signal 920 from operational amplifier 910 to lead 128 and/or lead 129. However, when input signal 916 exceeds clamping signal 918, operational amplifiers 906 and 908 and diodes 914 and 912 are biased such that pacing signal 920 will be the same value as clamping signal 920.

Accordingly, if clamping or suppression of electrical pacing pulses is desired, controller 104 may use processor 206 to send one or more control signals, such as clamping signal 918, to clamping circuit 400a (or 400b). For example, if processor 206 decides to suppress one or more electrical pacing pulses from signal generator 212, processor 206 may set clamping signal 918 to an appropriate value, such as 0 volts. In addition, if processor 206 detects that heart 102 requires assistance, then processor 206 may set clamping signal 918 to an appropriate value, such as 5-10 volts, such that electrical pacing pulses pass through clamping circuit 400a.

Other embodiments of the invention will be apparent to those skilled in the art from consideration of the specification and practice of the invention disclosed herein. For example, while one embodiment describes a three-chamber cardiac stimulation device, one of ordinary skill would appreciate that the present invention could be used in a four-chamber device, a two-chamber device, or even a single-chamber device having multiple intrachamber stimulation sites. Likewise, although FIGS. 2-4 illustrate sense amplifiers 200, 202, and 204, systems, methods and apparatus consistent with the present invention may use any desired number of sense amplifiers 200, 202, and 204. It is intended that the specification and examples be considered as exemplary only, with a true scope and spirit of the invention being indicated by the following claims.

The invention claimed is:

1. A cardiac pacemaker comprising:
   a first cardiac chamber lead branch to sense electrical activity in a first cardiac chamber of a heart and to deliver electrical stimulation to the first cardiac chamber;
   a second cardiac chamber lead branch to sense electrical activity in a second cardiac chamber of the heart and to deliver electrical stimulation to the second cardiac chamber;
   a controller to manage delivery of electrical pulses to at least one of the first cardiac chamber and the second cardiac chamber based on the electrical activity sensed by at least one of the first cardiac chamber lead branch and the second cardiac chamber lead branch;
   a signal generator, responsive to the controller, to generate the electrical pulses;
   a distributor circuit to distribute, responsive to a control signal from the controller, the electrical pulses from the signal generator to the first and second cardiac chambers via the first and second cardiac chamber lead branches;
   a first clamping circuit connected to the first cardiac chamber lead branch to reduce, under control of the controller, a voltage level of electrical pulses delivered through the first clamping circuit and the first cardiac chamber lead branch; and
   a second clamping circuit connected to the second cardiac chamber lead branch to reduce, under control of the controller, a voltage level of electrical pulses delivered through the second clamping circuit and the second cardiac chamber lead branch.

2. The cardiac pacemaker according to claim 1, wherein the distributor circuit includes electrical delay elements to delay delivery of the electrical pulses to one of the first and second cardiac chambers with respect to another of the first and second cardiac chambers.

3. The cardiac pacemaker according to claim 2, wherein the electrical delay elements are disposed in the first and second cardiac chamber lead branches.

4. The cardiac pacemaker according to claim 1, further comprising:
   a telemetry module to provide pacemaker diagnostic information to an external programmer via a radio link, and to program the cardiac pacemaker via the radio link.

5. The cardiac pacemaker according to claim 1, wherein the distributor circuit includes:
   a first transistor connected between the signal generator and the first cardiac chamber lead branch, and
   a second transistor connected between the signal generator and the second cardiac chamber lead branch,
   wherein gates of the first and second transistor are connected to the controller via a passive circuit to receive the control signal.

6. The cardiac pacemaker according to claim 1, wherein the controller controls the first and second clamping circuits to reduce the voltage level of the electrical pulses delivered therethrough when the controller detects spontaneous depolarization in the heart via at least one of the first and second cardiac chamber lead branches.

7. The cardiac pacemaker according to claim 6, wherein the clamping circuits suppress the electrical pulses when the controller detects spontaneous depolarization in the heart via at least one of the first and second cardiac chamber lead branches.

8. The cardiac pacemaker according to claim 1, wherein the distributor circuit includes:
   a passive delay circuit to receive the electrical pulses from the signal generator, the passive delay circuit having at least a first node and a second node,
   a first diode connected between the first node of the passive delay circuit and the first cardiac chamber lead branch to deliver the electrical pulses to the first cardiac chamber at a first instance in time, and
   a second diode connected between the second node of the passive delay circuit and the second cardiac chamber lead branch to deliver the electrical pulses to the second cardiac chamber at a second instance in time later than the first instance in time.

9. The cardiac pacemaker according to claim 8, wherein the passive delay circuit is an inductor-capacitor circuit.

10. The cardiac pacemaker according to claim 1, wherein the distributor circuit includes a switch to distribute the electrical pulses to the first and second cardiac chamber lead branches.

11. The cardiac pacemaker according to claim 10, wherein the distributor circuit further includes first and second shunt resistors respectively connected to the first and second cardiac chamber lead branches to set amplitude values of electrical pulses delivered to the first and second cardiac chambers.

* * * * *